US007795509B2

(12) United States Patent
Conkling et al.

(10) Patent No.: US 7,795,509 B2
(45) Date of Patent: *Sep. 14, 2010

(54) TOBACCO PRODUCTS WITH REDUCED NICOTINE

(75) Inventors: Mark A. Conkling, Fuquay Varina, NC (US); Wen Song, San Diego, CA (US); Nandini Mendu, Durham, NC (US)

(73) Assignee: North Carolina State University, Raleigh, NC (US)

(*) Notice: Subject to any disclaimer, the term of this patent is extended or adjusted under 35 U.S.C. 154(b) by 656 days.

This patent is subject to a terminal disclaimer.

(21) Appl. No.: 11/416,887

(22) Filed: May 3, 2006

(65) Prior Publication Data

US 2006/0200872 A1 Sep. 7, 2006

Related U.S. Application Data

(63) Continuation of application No. 10/356,076, filed on Jan. 31, 2003, now Pat. No. 7,304,220, which is a continuation of application No. 09/021,286, filed on Feb. 10, 1998, now Pat. No. 6,586,661.

(60) Provisional application No. 60/049,471, filed on Jun. 12, 1997.

(51) Int. Cl.
*C12N 15/29* (2006.01)
*C12N 15/54* (2006.01)
*C12N 15/82* (2006.01)
*A01H 5/00* (2006.01)
*A01H 5/10* (2006.01)

(52) U.S. Cl. .............. 800/317.3; 800/285; 800/286; 131/347; 131/352; 131/360; 131/366

(58) Field of Classification Search ............ 800/278, 800/298, 317.3; 131/352–358, 360, 366
See application file for complete search history.

(56) References Cited

U.S. PATENT DOCUMENTS

| 254,285 | A | 2/1882 | Forest |
|---|---|---|---|
| 299,541 | A | 6/1884 | Hearn |
| 2,479,526 | A | 8/1949 | Touton |
| 2,728,803 | A | 8/1955 | Helijo |
| 3,840,025 | A | 10/1974 | Fowler et al. |
| 3,905,123 | A | 9/1975 | Fowler et al. |
| 4,094,324 | A | 6/1978 | Bolsinger et al. |
| 4,192,323 | A | 3/1980 | Horne |
| 4,243,056 | A | 1/1981 | de la Burde et al. |
| 4,319,587 | A | 3/1982 | Moser |
| 4,372,208 | A | 2/1983 | Legardinier |
| 4,459,355 | A | 7/1984 | Cello et al. |
| 4,499,911 | A | 2/1985 | Johnson |
| 4,617,945 | A | 10/1986 | Vos et al. |
| 4,693,976 | A | 9/1987 | Schilperoort |
| 4,699,158 | A | 10/1987 | Sprinkel |
| 4,700,725 | A | 10/1987 | Geiszler |
| 4,751,348 | A | 6/1988 | Malmbert et al. |
| 4,762,785 | A | 8/1988 | Comai |
| 4,766,911 | A | 8/1988 | Oglesby |
| 4,795,855 | A | 1/1989 | Fillatti et al. |
| 4,821,747 | A | 4/1989 | Stuhl et al. |
| 4,835,162 | A | 5/1989 | Abood |
| 4,885,248 | A | 12/1989 | Ahlquist |
| 4,940,838 | A | 7/1990 | Schilperoort et al. |
| 4,943,674 | A | 7/1990 | Houck et al. |
| 4,945,050 | A | 7/1990 | Sanford et al. |
| 4,954,442 | A | 9/1990 | Gelvin et al. |
| 4,962,028 | A | 10/1990 | Bedbrook et al. |
| 4,966,916 | A | 10/1990 | Abood |
| 4,990,607 | A | 2/1991 | Katagirl et al. |
| 5,015,580 | A | 5/1991 | Christou et al. |
| 5,023,179 | A | 6/1991 | Lam et al. |
| 5,034,322 | A | 7/1991 | Rogers et al. |
| 5,035,252 | A * | 7/1991 | Mondre ................... 132/321 |
| 5,036,006 | A | 7/1991 | Sanford et al. |
| 5,062,434 | A | 11/1991 | Aulbach et al. |
| 5,097,025 | A | 3/1992 | Benfey et al. |
| 5,100,792 | A | 3/1992 | Sanford et al. |
| 5,107,065 | A | 4/1992 | Shewmaker et al. |
| 5,109,876 | A | 5/1992 | Hayden et al. |
| 5,149,645 | A | 9/1992 | Hoekema et al. |
| 5,157,115 | A | 10/1992 | Taniguchi |
| 5,177,308 | A | 1/1993 | Barton et al. |
| 5,179,022 | A | 1/1993 | Sanford et al. |

(Continued)

FOREIGN PATENT DOCUMENTS

CA    1341091    10/1984

(Continued)

OTHER PUBLICATIONS

Wu K. et al., Plant Physiology, 1997, vol. 114, pp. 1421-1431.*
Branch A.D. TIBS, Feb. 1998, pp. 45-50.*
Waterhouse P. et al., Trends in Plant Sciences, Nov. 1999, vol. 4, No. 11 pp. 452-457.*
Brunnemann et al. "Assessment of Carcinogenic Volatile N-Nitrosamines in Tobacco and in Mainstream and Sidestream Smoke from Cigarettes" *Cancer Research* 37:3218.3222 (977).
Collins et al. "Use of Anther-Derived Haploids in *Nicotiana*. I. Isolation of Breeding Lines Differing in Total Alkaloid Content" *Crop Sci.* 14:77-80 (1974).
Higo et al. "Plant cis-acting regulatory DNA elements (PLACE) database: 1999" *Nucleic Acids Research* 27:297-300 (1999).

(Continued)

*Primary Examiner*—Russell Kallis
(74) *Attorney, Agent, or Firm*—Myers Bigel Sibley & Sajovec, P.A.

(57) ABSTRACT

DNA encoding a plant quinolate phosphoribosyl transferase (QPRTase) enzyme, and constructs comprising such DNA are provided. Methods of altering quinolate phosphoribosyl transferase expression are provided.

16 Claims, 7 Drawing Sheets

U.S. PATENT DOCUMENTS

| | | | |
|---|---|---|---|
| 5,190,931 A | 3/1993 | Inouye et al. |
| 5,204,253 A | 4/1993 | Sanford et al. |
| 5,208,149 A | 5/1993 | Inouye et al. |
| 5,223,419 A | 6/1993 | Katagiri et al. |
| 5,229,292 A | 7/1993 | Stock et al. |
| 5,231,020 A | 7/1993 | Jorgensen et al. |
| 5,254,800 A | 10/1993 | Bird et al. |
| 5,260,205 A | 11/1993 | Nakatani et al. |
| 5,268,463 A | 12/1993 | Jefferson |
| 5,272,065 A | 12/1993 | Inouye et al. |
| 5,283,184 A | 2/1994 | Jorgensen et al. |
| 5,352,605 A | 10/1994 | Fraley et al. |
| 5,356,799 A | 10/1994 | Fabijanski et al. |
| 5,365,015 A | 11/1994 | Grierson et al. |
| 5,369,023 A | 11/1994 | Nakatani et al. |
| 5,371,015 A | 12/1994 | Sanford et al. |
| 5,377,697 A | 1/1995 | Deutsch et al. |
| 5,394,894 A | 3/1995 | Zade |
| 5,432,081 A | 7/1995 | Jefferson |
| 5,451,514 A | 9/1995 | Boudet et al. |
| 5,453,566 A | 9/1995 | Shewmaker et al. |
| 5,459,252 A | 10/1995 | Conkling et al. |
| 5,464,763 A | 11/1995 | Schilperoort et al. |
| 5,478,744 A | 12/1995 | Sanford et al. |
| 5,501,967 A | 3/1996 | Offringa et al. |
| 5,530,196 A | 6/1996 | Fraley et al. |
| 5,540,242 A | 7/1996 | Chao et al. |
| 5,580,722 A | 12/1996 | Foulkes et al. |
| 5,599,670 A | 2/1997 | Jefferson |
| 5,610,288 A | 3/1997 | Rubenstein |
| 5,626,152 A | 5/1997 | Davis et al. |
| 5,635,381 A | 6/1997 | Hooykaas et al. |
| 5,665,543 A | 9/1997 | Foulkes et al. |
| 5,668,295 A | 9/1997 | Wahab et al. |
| 5,683,985 A | 11/1997 | Chu et al. |
| 5,684,241 A * | 11/1997 | Nakatani et al. ......... 800/317.3 |
| 5,685,710 A | 11/1997 | Martinez Sagrera et al. |
| 5,693,512 A | 12/1997 | Finer et al. |
| 5,713,376 A | 2/1998 | Berger |
| 5,716,780 A | 2/1998 | Edwards et al. |
| 5,723,751 A | 3/1998 | Chua |
| 5,731,179 A | 3/1998 | Komari et al. |
| 5,759,829 A | 6/1998 | Shewmaker et al. |
| 5,767,378 A | 6/1998 | Bojsen et al. |
| 5,776,502 A | 7/1998 | Foulkes et al. |
| 5,776,771 A | 7/1998 | Yu et al. |
| 5,780,051 A | 7/1998 | Eswara et al. |
| 5,792,922 A | 8/1998 | Moloney |
| 5,796,500 A | 8/1998 | Hart |
| 5,803,081 A | 9/1998 | O'Donnell et al. |
| 5,810,020 A | 9/1998 | Northway et al. |
| 5,819,751 A | 10/1998 | Barnes et al. |
| 5,830,318 A | 11/1998 | Snow et al. |
| 5,830,728 A | 11/1998 | Christou et al. |
| 5,834,236 A | 11/1998 | Lamb et al. |
| 5,837,876 A | 11/1998 | Conkling et al. |
| 5,843,720 A | 12/1998 | Tangney et al. |
| 5,845,647 A | 12/1998 | O'Donnell |
| 5,846,720 A | 12/1998 | Foulkes et al. |
| 5,851,804 A | 12/1998 | Snyder et al. |
| 5,858,742 A | 1/1999 | Fraley et al. |
| 5,858,774 A | 1/1999 | Malbon et al. |
| 5,862,750 A | 1/1999 | Dell'Olmo |
| 5,863,733 A | 1/1999 | Foulkes et al. |
| 5,877,023 A | 3/1999 | Sautter et al. |
| 5,929,306 A | 7/1999 | Torisky et al. |
| 5,932,782 A | 8/1999 | Bidney |
| 5,962,768 A | 10/1999 | Cornelissen et al. |
| 5,976,793 A | 11/1999 | Foulkes et al. |
| 5,976,880 A | 11/1999 | Sautter et al. |
| 5,981,839 A | 11/1999 | Knauf et al. |
| 5,989,915 A | 11/1999 | Christou et al. |
| 5,994,629 A | 11/1999 | Bojsen et al. |
| 6,020,969 A | 2/2000 | Struckhoff et al. |
| 6,022,863 A | 2/2000 | Peyman |
| 6,051,409 A | 4/2000 | Hansen et al. |
| 6,051,757 A | 4/2000 | Barton et al. |
| 6,060,310 A | 5/2000 | Cho-Chung |
| 6,077,992 A | 6/2000 | Yadav |
| 6,135,121 A | 10/2000 | Williams |
| 6,136,799 A | 10/2000 | Foulkes et al. |
| 6,153,811 A | 11/2000 | Lowe et al. |
| 6,165,712 A | 12/2000 | Foulkes et al. |
| 6,165,715 A | 12/2000 | Collins et al. |
| 6,166,032 A | 12/2000 | Viner |
| 6,174,724 B1 | 1/2001 | Rogers et al. |
| 6,191,258 B1 | 2/2001 | Lamb et al. |
| 6,197,827 B1 | 3/2001 | Cary |
| 6,203,976 B1 | 3/2001 | Foulkes et al. |
| 6,255,560 B1 | 7/2001 | Fraley et al. |
| 6,262,033 B1 | 7/2001 | Morishita et al. |
| 6,265,638 B1 | 7/2001 | Bidney et al. |
| 6,271,031 B1 | 8/2001 | Falco et al. |
| 6,279,475 B1 | 8/2001 | Cardoso |
| 6,281,410 B1 | 8/2001 | Knauf et al. |
| 6,202,649 B1 | 10/2001 | Williams |
| 6,303,847 B1 | 10/2001 | Kawaoka et al. |
| 6,350,479 B1 | 2/2002 | Williams et al. |
| 6,423,520 B1 | 7/2002 | Conkling et al. |
| 6,425,401 B1 | 7/2002 | Williams |
| RE38,123 E | 5/2003 | Williams |
| 6,557,560 B2 | 5/2003 | Kastner |
| 6,584,981 B2 | 7/2003 | Hampl, Jr. |
| 6,586,661 B1 * | 7/2003 | Conkling et al. ......... 800/317.3 |
| 6,907,887 B2 * | 6/2005 | Conkling ................ 131/364 |
| 6,911,541 B2 | 6/2005 | Conkling |
| 2001/0006797 A1 | 7/2001 | Kumagai et al. |
| 2001/0026941 A1 | 10/2001 | Held et al. |
| 2002/0108151 A1 | 8/2002 | Conkling et al. |
| 2002/0174874 A1 | 11/2002 | Williams |
| 2002/0197688 A1 | 12/2002 | Pandolfino |
| 2003/0018997 A1 | 1/2003 | Conkling et al. |
| 2004/0031074 A1 | 2/2004 | Conkling et al. |
| 2004/0103454 A1 | 5/2004 | Conkling et al. |
| 2004/0168211 A1 | 8/2004 | Conkling et al. |
| 2006/0057723 A1 | 3/2006 | Conkling et al. |

FOREIGN PATENT DOCUMENTS

| | | |
|---|---|---|
| CA | 2032443 | 6/1990 |
| CA | 2325344 | 10/1998 |
| CA | 2248622 | 3/1999 |
| CA | 1341091 | 9/2000 |
| DE | 1917552 | 4/1969 |
| DE | 2203105 | 1/1972 |
| EP | 0 116 718 A1 | 8/1984 |
| EP | 0 120 515 A2 | 10/1984 |
| EP | 0 120 515 B1 | 10/1984 |
| EP | 0 120 516 A2 | 10/1984 |
| EP | 0 120 516 B1 | 10/1984 |
| EP | 0 131 620 B1 | 1/1985 |
| EP | 0 131 623 B1 | 1/1985 |
| EP | 0 131 623 B2 | 1/1985 |
| EP | 0 131 624 B1 | 1/1985 |
| EP | 0 140 308 A2 | 5/1985 |
| EP | 0 140 308 A3 | 5/1985 |
| EP | 0 140 308 B1 | 5/1985 |
| EP | 0 140 308 B2 | 5/1985 |
| EP | 0 159 779 B1 | 10/1985 |
| EP | 0 176 112 B1 | 4/1986 |
| EP | 0 189 707 B1 | 8/1986 |
| EP | 0 223 399 A1 | 5/1987 |
| EP | 0 223 399 B1 | 5/1987 |
| EP | 0 224 287 A1 | 6/1987 |

| | | |
|---|---|---|
| EP | 0 240 208 A2 | 10/1987 |
| EP | 0 240 208 A3 | 10/1987 |
| EP | 0 240 208 B1 | 10/1987 |
| EP | 0 265 556 A1 | 5/1988 |
| EP | 0 270 822 A1 | 6/1988 |
| EP | 0 290 799 | 11/1988 |
| EP | 0 290 799 A2 | 11/1988 |
| EP | 0 290 799 A3 | 11/1988 |
| EP | 0 320 500 A2 | 6/1989 |
| EP | 0 320 500 A3 | 6/1989 |
| EP | 0 131 623 B1 | 3/1991 |
| EP | 0 131 623 B2 | 3/1991 |
| EP | 0 458 367 A1 | 11/1991 |
| EP | 0 458 367 B1 | 11/1991 |
| EP | 0 467 349 B1 | 1/1992 |
| EP | 0 486 214 A2 | 5/1992 |
| EP | 0 486 214 A3 | 5/1992 |
| EP | 0 486 234 B1 | 5/1992 |
| EP | 0 647 715 | 4/1995 |
| EP | 0 818 532 A1 | 1/1998 |
| EP | 1 457 562 | 9/2004 |
| EP | 1 457 563 | 9/2004 |
| WO | WO 84/02913 | 8/1984 |
| WO | WO 84/ 02913 | 8/1984 |
| WO | WO 84/02919 | 8/1984 |
| WO | WO 84/ 02919 | 8/1984 |
| WO | WO 84/02920 | 8/1984 |
| WO | WO 84/ 02920 | 8/1984 |
| WO | WO 90/12084 | 10/1990 |
| WO | WO 91/01379 | 2/1991 |
| WO | WO 91/02070 | 2/1991 |
| WO | WO 91/11535 | 8/1991 |
| WO | WO 91/13992 | 9/1991 |
| WO | WO 91/14790 | 10/1991 |
| WO | WO 92/15680 | 9/1992 |
| WO | WO 92/18522 | 10/1992 |
| WO | WO 92/19732 | 11/1992 |
| WO | WO 93/05163 | 3/1993 |
| WO | WO 93/05646 | 4/1993 |
| WO | WO 93/14768 | 8/1993 |
| WO | WO 93/17116 | 9/1993 |
| WO | WO 94/20627 | 9/1994 |
| WO | WO 94/26913 | 11/1994 |
| WO | WO 94/28142 | 12/1994 |
| WO | WO 94/28142 A | 12/1994 |
| WO | WO 95/11687 | 5/1995 |
| WO | WO 95/12415 | 5/1995 |
| WO | WO 95/16031 | 5/1995 |
| WO | WO 95/16031 | 6/1995 |
| WO | WO 95/34668 | 12/1995 |
| WO | WO 95/35388 | 12/1995 |
| WO | WO 96/21725 | 7/1996 |
| WO | WO 97/05261 | 2/1997 |
| WO | WO 97/08330 | 3/1997 |
| WO | WO 97/12046 | 4/1997 |
| WO | WO 97/32016 | 9/1997 |
| WO | WO 97/38723 | 10/1997 |
| WO | WO 97/41892 | 11/1997 |
| WO | WO 97/44064 | 11/1997 |
| WO | WO 97/44450 | 11/1997 |
| WO | WO 97/49727 | 12/1997 |
| WO | WO 98/05226 | 2/1998 |
| WO | WO 98/05757 | 2/1998 |
| WO | WO 98/30701 | 7/1998 |
| WO | WO 98/32843 | 7/1998 |
| WO | WO 98/56923 | 12/1998 |
| WO | WO 99/10512 | 3/1999 |
| WO | WO 99/13085 | 3/1999 |
| WO | WO 99/14348 | 3/1999 |
| WO | WO 99/25854 | 5/1999 |
| WO | WO 99/26634 | 6/1999 |
| WO | WO 99/32619 | 7/1999 |
| WO | WO 99/32642 | 7/1999 |
| WO | WO 99/49029 | 9/1999 |
| WO | WO 99/53050 | 10/1999 |
| WO | WO 99/61631 | 12/1999 |
| WO | WO 00/12735 | 3/2000 |
| WO | WO 00/18939 | 4/2000 |
| WO | WO 00/29566 | 5/2000 |
| WO | WO 00/37060 | 6/2000 |
| WO | WO 00/37663 | 6/2000 |
| WO | WO 00/55333 | 9/2000 |
| WO | WO 00/63398 | 10/2000 |
| WO | WO 00/67558 | 11/2000 |
| WO | WO 01/09302 | 2/2001 |
| WO | WO 01/38514 | 5/2001 |
| WO | WO 01/44482 | 6/2001 |
| WO | WO 01/49844 | 7/2001 |
| WO | WO 01/51630 | 7/2001 |
| WO | WO 01/51630 A1 | 7/2001 |
| WO | WO 01/68836 | 9/2001 |
| WO | WO 01/68836 A2 | 9/2001 |
| WO | WO 01/77350 | 10/2001 |
| WO | WO 01/77350 A2 | 10/2001 |
| WO | WO 02/00927 | 1/2002 |
| WO | WO 02/18607 | 3/2002 |
| WO | WO 02/38588 | 5/2002 |
| WO | WO 02/100199 | 12/2002 |
| WO | WO 2005/018307 | 3/2005 |

OTHER PUBLICATIONS

Leete et al. "Biosynthesis and Metabolism of the Tobacco Alkaloids" In *Alkaliods: Chemical and Biological Perspectives*, S.W. Pelletier, ed., John Wiley & Sons, pp. 85-152 (1983).

Legg et al. "Inheritance of Per Cent Total Alkaloids in *Nicotiana Tabacum* L. II Genetic Effects of Two Loci in Burley 21 X LA Burley 21 Populations" *Can J Genet Cytol.* 13:287-91 (1971).

Rombauts et al. "PlantCARE, a plant cis-acting regulatory element database" *Nucleic Acids Research* 27:295-296 (1999).

Schroth et al. "Tobacco-Specific Nitrosamines," Research and Development, Neuchatel-Quarterly Report, pp. 1-8, Apr.-Jun. 1994.

Shillito et al. "Direct Gene Transfer to Protoplasts of Dicotyledonous and Monocotyledonous Plants by a Number of Methods, Including Electroporation" *Methods Enzymol.* 153:313-36 (1987).

Watson "Nicotine free and flavorful too" in The Buffalo News, p. A9 and p. A15, Sep. 7, 1997 (newspaper article).

Adams et al. "Tobacco-Specific Nitrosamine Accumulation in Different Genotypes of Burley Tobacco at Different Stages of Growth and Air-Curing" TCRC (35 pages)(1987).

Branch. "A Good Antisense Molecule is Hard to Find" *TIBS* 23:45-50 (1998).

Brunnemann et al. "Recent Advances in Tobacco Science: Analytical Studies on N-Nitrosamines in Tobacco and Tobacco Smoke" Proceedings of a Symposium Presented at the 45th Meeting of the Tobacco Chemists' Research Conference, vol. 17 pp. 71-112, Oct. 20-23, 1991, The Grove Park Inn, Asheville, North Carolina.

Burton et al. "Burley Tobacco—The Effects of Harvesting and Curing Procedures on the Composition of the Cured Leaf" *Tobacco Science* 5:48-53 (1988).

Chamberlain et al. "Curing Effects on Contents of Tobacco Specific Nitrosamines in Bright and Burley Tobaccos" USDA, ARS pp. 1-41 (1986).

Feth et al. "Regulation in Tobacco Callus of Enzyme Activities of the Nicotine Pathway" *Planta* 168:402-407 (1986).

Harris. "Smoke Yields of Tobacco-Specific Nitrosamines in Relation to FTC Tar Level and Cigarette Manufacturer: Analysis of the Massachusetts Benchmark Study" *Public Health Reports* 116:336-343 (2001).

Hecht et al. "Environmental Carcinogens Selected Methods of Analysis. II.2 Tobacco and Tobacco Smoke (Volatile and Tobacco-Specific Nitrosamines). II.2.d Tobacco-Specific Nitrosamines in Tobacco and Tobacco Smoke" *World Health Organization*, International Agency for Research on Cancer, IARC Publications 45:93-101 (1983).

Hecht et al. "Environmental Carcinogens Selected Methods of Analysis. IV.6 HPLC-TEA of Tobacco Specific Nitrosamines" *World Health Organization*, International Agency for Research on Cancer, IARC Publications 45:249-436 (1983).

Hecht et al. "The Metabolism of Cyclic Nitrosamines" *ACS Symposium Series* 174(4):49-75 (1981).

Hoffman et al. "Environmental Carcinogens Selected Methods of Analysis. II.2 Tobacco and Tobacco Smoke (Volatile and Tobacco-Specific Nitrosamines). II.2.b Volatile Nitrosamines in Tobacco and Mainstream and Sidestream Smoke and Indoor Environments" *World Health Organization*, International Agency for Research on Cancer, IARC Publications 45:69-83 (1983).

Legg et al. "Inheritance of Percent Total Alkaloids in *Nicotiana tabacum* L." *J. Hered.* 60:213-217 (1969).

Mingwu. "The Source and the Regulation of Nitrogen Oxide Production for Tobacco-Specific Nitrosamine Forming During Air-Curing Tobacco" Disseration, University of Kentucky (206 pages) (1998).

Sinclair et al. "Analysis of Wound-Induced Gene Expression in *Nicotiana* Species With Contrasting Alkaloid Profiles" *Functional Plant Biology* 31:721-729 (2004).

Sinclair et al. "Molecular Characterization of Quinolate Phosphoribosyltransferase (QPRTase) in *Nicotiana*" *Plant Molecular Biology* 44:603-617 (2000).

Stepanov et al. "Tobacco-Specific Nitrosamines in New Tobacco Products" *Nicotine & Tobacco Research* 8(2):309-313 (2006).

Tricker et al. "Topics Related to N-Nitrosamines and Their Precursors" 45th TCRC (5 pages)(Oct. 20-23, 1991).

Assignment by Mark Conkling, Nandini Mendu and Wen Song to NCSU of U.S. Appl. No. 09/021,286, filed Feb. 10, 1998 (4 pages)(executed May 12 and 13, 1998) and recorded with the U.S. Patent and Trademark Office on May 22, 1998 on Reel 009206, Frame 0761.

Star Scientific publication entitled "StarCure Technology" (2 pages)(Apr. 30,1999).

Ward. "Process May Cut Cigarettes' Cancer Risk" The Courier Journal. Louisville, KY (2 pages)(Apr. 30, 1999).

Employee Non-Disclosure/Non-Competition and Invention Assignment Agreement between Vector Tobacco (USA) Ltd. and Dr. Mark Conkling executed Sep. 12, 2000 and recorded with the U.S. Patent and Trademark Office on Aug. 25, 2006 at Reel No. 018171, Frame No. 0988 (6 pages).

Assignment by Dr. Mark Conkling to NCSU of tobacco variety Vector Burley 21-41 (2 pages)(executed Nov. 27, 2000).

Plant Variety Protection Application for Vector Burley 21-41, filed by NCSU on Dec. 4, 2000. (24 pages).

Assignment by Mark Conkling and Yan Li to NCSU of U.S. Appl. No. 09/941,042 filed Aug. 28, 2001, (3 pages)(executed Mar. 11, 2002) and recorded with the U.S. Patent and Trademark Office on Mar. 20, 2002 on Reel 012710, Frame 0180.

Plant Variety Certificate No. 200100039 to NCSU for Vector 21-41 by the USDA (1 page) (Sep. 16, 2003).

Vector Tobacco (USA) Ltd. "Changing the Future of Tobacco" Pamphlet for farmers. (18 pages) (Jan. 3, 2001).

Fairclough. "Vector Develops Cigarette With Almost No Nicotine" The Wall Street Journal (2 pages) (Jan. 16, 2001).

Zawada. "Vector Makes Nearly Nicotine-Free Tobacco; Company Will Market it as a Way for Smokers to Overcome Addiction" *Winston-Salem Journal* (1 page) (Jan. 17, 2001).

Business Wire Press Release. "Vector Group Reduces Cancer Causing Agent in Cigarettes to Below the Level That Initiates Carcinomas" (3 pages) (Feb. 13, 2001).

Fairclough. "Vector Vows to Beat Competitors in Race to Produce 'Safer' Cigarette" The Wall Street Journal (8 pages) (Feb. 13, 2001).

Annual Report (SEC Form 10-K) filed by Vector Group Ltd. with the United States Securities and Exchange Commission for fiscal year ending Dec. 31, 2000 (238 pages) (filed Apr. 2, 2001).

"Application for Determination of Nonregulatory Status for Vector 21-41: Reduced-Nicotine Tobacco" submitted by Vector Tobacco (USA) Ltd. (34 pages) (Apr. 27, 2001).

Business Wire Press Release. "Vector Group Condemns Proposed North Carolina Legislation; Bill Would Criminalize the Production of Vector's New Nicotine Free Cigarettes" (2 pages) (May 8, 2001).

Vector Group Ltd. Press Release. "Vector Group Raises $100 Million in Private Equity and Debt Placements. Proceeds to Fund Advertising and Promotion of New Omni™ Cigarette Products" (1 page) (May 16, 2001).

U.S. Appl. No. 60/296,347, titled "Tobacco Biomass Utilization" and listing Mr. Joseph Pandolfino as inventor (31 pages) (filed Jun. 6, 2001).

"Petition for Determination of Regulatory Status" (1 page) and "Application for Determination of Nonregulated Status for Vector 21-41 Reduced-Nicotine Tobacco" Revised application filed by Vector Tobacco (USA) Ltd. (69 pages) (Aug. 31, 2001).

Annual Report (SEC Form 10-K) filed by Vector Group Ltd. with the United States Securities and Exchange Commission for fiscal year ending Dec. 31, 2001 (211 pages) (Filed Apr. 1, 2002).

"Approval of Vector Tobacco (USA) Ltd. Petition (01-121-01p) Seeking a Determination of Non-regulated Status for Reduced-nicotine Tobacco Line Vector 21-41" (36 pages) (Sep. 16, 2002).

Federal Register Notice Entitled "Vector Tobacco: Availability of Determination of Nonregulated Status for Tobacco Genetically Engineered for Reduced Nicotine" vol. 67 No. 232 (2 pages) (Dec. 3, 2002).

Assignment by Dr. Mark Conkling to Vector Tobacco Ltd. of U.S. Appl. No. 10/729,121, filed Dec. 5, 2003 (1 page) (executed Apr. 7, 2004) and recorded with the U. S. Patent and Trademark Office on Apr. 12, 2004.

Xie et al. "Biotechnology: A Tool for Reduced-Risk Tobacco Products —The Nicotine Experience from Test Tube to Cigarette Pack" 58th Tobacco Science Research Conference, pp. 17-37 (2004).

Wu et al. "The Arabidopsis 14-3-3 Multigene Family" *Plant Physiol.* 114:1421-14318 (1997).

Chang et al. "Gene Expression from Both Intronless and Intron-Containing *Rous sarcoma* Virus Clones is Specifically Inhibited by Anti-Sense RNA" *Molecular and Cellular Biology* 5(9):2341-2348 (1985).

De Block et al. "Expression of Foreign Genes in Regenerated Plants and in Their Progeny" *EMBO Journal* 3(8):1681-1689 (1984).

Feth et al. "Determination of Putrescine N-methyltransferase by High Performance Liquid Chromatography" *Phytochemistry* 24(5):921-923 (1985).

Lagrimini et al. "Peroxidase-Induced Wilting in Transgenic Tobacco Plants" *The Plant Cell* 2:7-18 (1990).

Mizusaki et al. "Phytochemical Studies on Tobacco Alkaloids XIV. The Occurrence and Properties of Putrescine N-methyltransferase in Tobacco Roots" *Plant & Cell Physiology* 12:633-640 (1971).

Napoli et al. "Introduction of a Chimeric Chalcone Synthase Gene into *Petunia* Results in Reversible Co-Suppression of Homologous Genes in trans" *The Plant Cell* 2:279-289 (1990).

Burtin, D., et al., Over expression of Arginine Decarboxylase in Transgenic Plants, *Biochem. J.*, vol. 325 (Part 2), pp. 331-337 (1997).

Bush, et al., Nicotine Biosynthetic Enzymes of Burley Tobacco, *Tobacco Abstracts*, vol. 24, p. 260. (1980).

Bush, et al., Physiological Aspects of Genetic Variation in Nicotine Content in Tobacco (*Nicotiana tabacum*), *Tobacco Abstract*, vol. 23, p. 30 (1979).

Conkling, et al., Isolation of transcriptionally regulated root-specific genes from tobacco; *Plant Physiology*, vol. 93, No. 3, pp. 1203-1211 (1990).

Cornelissen, et al., Both RNA Level and Translation Efficiency are Reduced by Anti-Sense RNA in Transgenic Tobacco, *Nucleic Acids Res.*, vol. 17, No. 3., pp. 833-843 (1989).

Crowley, et al., *Cell.* vol. 43, pp. 633-641 (1985).

Cuozzo, et al., Viral Protection in Transgenic Tobacco Plants Expressing the *Cucumber mosaic* Virus Coat Protein or Its Antisense RNA, *Biotechnology*, vol. 6, pp. 549-557 (1988).

Delauney, et al., A Stable Bifunctional Antisense Transcript Inhibiting Gene Expression in Transgenic Plants, *Proc. Natl. Acad. Sci. USA*, vol. 85, pp. 4300-4304 (1988).

Ecker, et. al., Inhibition of Gene Expression in Plant Cells by Expression of Antisense RNA, *Proc. Natl. Acad. Sci. USA*, vol. 83, pp. 5372-5376 (1986).

Feth, et al., Regulation in Tobacco Callus or Enzyme Activities of the Nicotine Pathway, *Planta*, vol. 168, pp. 402-407, Sep. 1986.

Hamill, et al.; Over-expressing a yeast ornthine decarboxylase gene in transgenic roots of *Nicotiana rustica* can lead to enhanced nicotine accumulation, *Plant Molecular Biology*, vol. 15, pp. 27-38 (1990).

Hemenway, et al., Analysis of the Mechanism of Protection in Transgenic Plants Expressing the Potato Virus x Coat Protein or Its Antisense RNA, *EMBO J.*, vol. 7, pp. 1273-1280, May 1998.

Hibi, et al., Gene Expression in Tobacco Low-Nicotine Mutants, *Plant Cell*, vol. 6, pp. 723-735 (1994).

Holmberg, et al.; Transgenic tobacco expressing Vitreoscilla hemoglobin exhibits enhanced growth and altered metabolite production, *Nature Biotechnology*, vol. 15, pp. 244-247 (1997).

Hughes, Kelly T., et al., The *Salmonella typhimurium* nadC Gene: Sequence Determination by Use of Mud-P22 and Purification of Quinolinate Phosphoribosyltransferase, *Journal of Bacteriology*, vol. 175, No. 2, pp. 479-486 (Jan. 1993).

Izant, et al., Constitutive and conditional Suppression of Exogenous and Endogenous Genes by Anti-Sense RNA, *Science*, vol. 229, pp. 345-352 (1985).

Izant, et al., Inhibition of Thymidine Kinase Gene Expression by Anti-Sense RNA: A Molecular Approach to Genetic Analysis, *Cell*, vol. 36, pp. 1007-1015 (Apr. 1984).

Kim, et al., Stable Reduction of Thymidine Kinase Activity in Cells Expressing High Levels of Anti-Sense RNA, *Cell*, vol. 42, pp. 129-138 (Aug. 1985).

Lam, et al., Site-Specific Mutations After In Vitro Factor Binding and Change Promoter Expression Pattern in Transgenic Plants, *Proc. Nat. Acad. Sci. USA*, vol. 86, pp. 7890-7894 1989.

Lichtenstein, Anti-sense RNA As A Tool To Study Plant Gene Expression, *Nature*, vol. 333, pp. 801-802 (1988).

McGarry, et al., *Proc. Natl. Acad. Sci. USA* (1986).

Melton, Injected Anti-Sense RNAs Specifically Block Messenger RNA Translation in Vivo, *Proc. Natl. Acad. Sci. USA*, vol. 82, pp. 144-148 (1985).

Mizuno, et al., A Unique Mechanism Regulating Gene Expression: Translational Inhibition By a Complementary RNA Transcript (micRNA), *Trends in Genetics*, vol. 1, pp. 22-25 (1985).

Ohta, et al., Metabolic Key Step Discriminating Nicotine Producing *Tobacco callus* Strain From Ineffective One, *Biochem. Physiol. Pflanzen*, vol. 175, pp. 382-385 (1980).

Pestka, et al., Anti-mRNA: Specific Inhibition of Translation of Single mRNA Molecules, *Proc. Natl. Acad. Sci. USA*, vol. 81, pp. 7525-7528 (1984).

Poulsen, et al., Dissection of 5' Upstream Sequences for Selective Expression of the *Nicotiana plumbaginifolia* rbcS-8B gene, *Mol. Gen. Genet.*, vol. 214, pp.-16-23 (1988).

Preiss, et al., Molecular genetics of Krüppel, A Gene Required for Segmentation of the *Drosphila* Embryo, *Plant Molecular Biology*, vol. 11, pp. 463-471 (1988).

Rezaian, et al., Anti-Sense RNAs of *Cucumber mosaic* Virus in Transgenic Plants Assessed For Control of the Virus, *Plant Molecular Biology*, vol. 11, pp. 463-471 (1988).

Rodermel, et al., Nuclear-Organelle Interactions: Nuclear Antisense Gene Inhibits Ribulose Biphosphate Carboxylase Enzyme Levels in Transformed Tobacco Plants, *Cell*, vol. 55, pp. 673-681 (1988).

Rosenberg, et al., Production of Phenocopies by Krüppel Antisense RNA Injection Into *Drosophila* Embryos, *Nature*, vol. 313, pp. 703-706 (1985).

Rothstein, et al., Stable and Heritable Inhibition of the Expression of Nopaline Synthase in Tobacco Expressing Antisense RNA, *Proc. Natl. Sci. USA*, vol. 84, pp. 8439-8443 (1987).

Sandler, et al., Inhibition of Gene Expression in Transformed Plants by Antisense RNA, *Plant Molecular Biology*, vol. 11, pp. 301-310 (1988).

Saunders, et al., Comparison of Nicotine Biosynthetic Enzymes in Nicotine Level Genotypes of Burley Tobacco, *Agronomy Abstracts*, p. 84 (1978).

Saunders, et al., Enzyme Activites in Nicotine Biosynthesis in *Nicotiana tabacum*, *Journal of National Products*, vol. 41, p. 646, 1978.

Sheehey, et al., Reduction of Polygalacturonase Activity in Tomato Fruit by Antisense RNA; *Proc. Natl. Acad. Sci, USA*, vol. 85, pp. 8805-8809 (1988).

Smith, et al., Antisense RNA Inhibition of Polygalacturonase Gene Expression in Transgenic Tomatoes, *Nature*, vol. 334, pp. 724-726 (1988).

Song, Wen, Molecular characterizations of two tobacco root-specific genes: TobRB7 and NtQPT1(1997); *UMI*, Order No. DA9804246 from: Diss. Abstr. Int., B, vol. 58, No. 8, pg. 4061; 224 pp. available; XP002080228.

Travers, Regulation by Anti-Sense RNA, *Nature*, vol. 310, p. 410 (1984).

Van der Krol, et al., An Anti-Sense Chalcone Synthase Gene in Transgenic Plants Inhibits Flower Pigmentation, *Nature*, vol. 333, pp. 866-869 (1988).

Van der Krol, et al., Antisense Genes in Plants; An Overview, *Gene*, vol. 72, pp. 45-50 (1988).

Van der Krol, et al., Modulation of Eukaryotic Gene Expression by Complementary RNA or DNA Sequences, *Biotechniques*, vol. 6, pp. 958-976 (1988).

Wagner, et al., Regulation in *Tobacco callus* of Enzyme Activities of the Nicotine Pathway, *Planta*, vol. 168, pp. 408-412. 1986.

Wagner, et al., The Regulation of Enzyme Activities of the Nicotine Pathway in Tobacco, *Physiol. Plantarum*, vol. 68, pp. 667-672 (1986).

Wagner, Roland, et al., Determination of Quinolinic Acid Phosphoribosyl-Transferase in Tobacco, *Phytochemistry*, vol. 23, No. 9, pp. 1881-1883 (1884).

Weintraub, et al., Anti-sense RNA as a Molecular Tool for Genetic Analysis, *Trends in Genetics*, vol. 1, pp. 22-25 (1985).

West, et al., Duplex-Duplex Interactions Catalyzed by RecA Protein Allow Strand Exchanges to Pass Double-Strand Breaks in DNA, *Cell*, pp. 683-691 (1984).

Chang et al. "Gene Expression from Both Intronless and Intron-Containing *Rous sarcoma* Virus Clones is Specifically Inhibited by Anti-Sense RNA" *Molecular and Cellular Biology* 5(9):2341-2348 (1985).

DeBlock et al. "Expression of Foreign Genes in Regenerated Plants and in Their Progeny" *EMBO Journal* 3(8):1681-1689 (1984).

Feth et al. "Determination of Putrescine N-methyltransferase by High Performance Liquid Chromatography" *Phytochemistry* 24(5):921-923 (1985).

Feth et al. "Regulation in Tobacco Callus of Enzyme Activities of the Nicotine Pathway I. The Route Ornithine to Methylpyrroline" *Planta* 168:402-407 (1986).

Lagrimini et al. "Peroxidase-Induced Wilting in Transgenic Tobacco Plants" *The Plant Cell* 2:7-18 (1990).

Mizusaki et al. "Phytochemical Studies on Tobacco Alkaloids XIV. The Occurrence and Properties of Putrescine N-methyltransferase in Tobacco Roots" *Plant & Cell Physiology* 12:633-640 (1971).

Napoli et al. "Introduction of a Chimeric Chalcone Synthase Gene into Petunia Results in Reversible Co-Suppression of Homologous Genes in trans" *The Plant Cell* 2:279-289 (1990).

Rothstein et al. "Stable and heritable Inhibition of the Expression of Nopaline Synthase in Tobacco Expressing Antisense RNA" *Proceedings of the National Academy of Science, USA* 84:8439-8443 (1987).

Wagner et al. "The Regulation of Enzyme Activities of the Nicotine Pathway in Tobacco" *Physiol Plantarum* 68:667-672 (1986).

Abeyama et al. "A role for NF-κB-Dependent Gene Transactivation in Sunburn" *The Journal of Clinical Investigation* 105(12):1751-1759 (Jun. 2000).

Adam et al. (1995) "Transcription of tobacco phytochrome-A genes initiates at multiple start sites and requires multiple *cis*-acting regulatory elements" *Plant Mol. Biol.* 29(5):983-993.

Akimoto et al. "Growth Inhibition of Cultured Human Tenon's Fibroblastic Cells by Targeting the E2F Transctiption Factor" *Exp. Eye Res.* 67:395-401 (1998).

Aparicio et al. (2001) "Recognition of *cis*-acting sequences in RNA 3 of *Prunus necrotic ringspot* virus by the replicase of *Alfalfa mosaic virus*" *J. Gen. Virol.* 82(Pt 4):947-951.

Beck et al. "Nucleotide Sequence and Exact Localization of the Neomycin Phosphotransferase Gene from Transposon Tn 5" *Gene*, 19:327-336 (1982).

Bevan & Flavell "A Chimaeric Antibiotic Resistance Gene as a Selectable Marker for Plant Cell Transformation" *Nature* 304:184-187 (1983).

Bogusz et al. "Functioning haemoglobin Genes in Non-Nodulating Plants" *Nature* 331:178-180 (1988).

Borisjuk et al. (2000) "Tobacco ribosomal DNA spacer element stimulates amplification and expression of heterologous genes" *Nat. Biotechnol.* 18(12):1303-1306.

Bustos et al. (1989) Regulation of β-glucuronidase expression in transgenic tobacco plants by an A/T-rich, *cis*-acting sequence found upstream of a French bean β-phaseolin gene. *Plant Cell* 1(9):839-853.

Chilton et al. "Tailoring the Agrobacterium Ti Plasmid as a Vector for Plant Genetic Engineering" *Stadler Symp.* 13:39-53 (1981).

Clusel et al. (1995) Inhibition of HSV-1 proliferation by decoy phosphodiester oligonucleotides containing ICP4 recognition sequences. *Gene Expr.* 4(6):301-309.

Colbere-Garapin et al. "A New Dominant Hybrid Selective Marker for Higher Eukaryotic Cells" *J. Mol. Biol.* 150:1-14 (1981).

D'Acquisto et al. "Local Administration of Transcription Factor Decoy Oligonucleotides to Nuclear Factor-κB Prevents Carrageenin-Induced Inflammation in Rat Hind Paw" Gene Therapy 7:1731-1737 (2000) (Abstract only).

Database EMBL Online! EBI; *A. thaliana*, clone TAP0198, March 5, 1996, Accession No. F20096, 2 pages.

GenBank Accession No. AC097498 *Homo sapiens* BAC clone RP11-326N15 from 4 (2000).

GenBank Accession No. AC105416 *Homo sapiens* BAC clone RP11-310A13 from 4 (2000).

GenBank Accession No. U08931 *Nicotiana tabacum* cryptic seed coat-specific promoter (1994).

Davies and Jimenez "A New Selective Agent for Eukaryotic Cloning Vectors" *Am. J. Trop. Med. Hyg.* 29(5):1089-1092 (1980).

Depicker et al., "Nopaline Synthase: Transcript Mapping and DNA Sequence", Journal of Molecular and Applied Genetics, 1(6): 561-573 (1982).

Ehsan et al (2001) "Long-term stabilization of vein graft wall architecture and prolonged resistance to experimental atherosclerosis after E2F decoy oligonucleotide gene therapy" *J. Thorac. Cardiovasc. Surg.* 121(4):714-722.

Evans et al. Distribution of Root in mRNA Species in Other Vegetative Organs of Pea (*Pisum sativum* L.) *Mol. Gen. Genet.* 214:153-157 (1988).

Fobert et al. "T-DNA Tagging of a Seed Coat-Specific Cryptic Promoter in Tobacco" *Plant Journal* 6(4):567-577 (1994).

Fraley et al. "Expression of Bacterial Genes in Plant Cells" *Proc. Natl. Acad. Sci. USA*, 80:4803-4807 (1983).

Fraley et al. "Use of a Chimeric Gene to Confer Antibiotic Resistance to Plant Cells", *Advances in Gene Technology: Molecular Genetics of Plants and Animals*, 20:211-221 (1983).

Framond et al. "Mini-Ti: A New Vector Strategy for Plant Genetic Engineering", *BIO/TECHNOLOGY* 5:262-269 (1983).

Fuller et al. "Soybean Nodulin Genes: Analysis of cDNA Clones Reveals Several Major Tissue-Specific Sequences in Nitrogen-Fixing Root Nodules" *Proc. Natl. Acad. Sci. USA* 80:2594-2598 (1983).

Geffers et al. (2000) "Anaerobiosis-specific interaction of tobacco nuclear factors with *cis*-regulatory sequences in the maize *GapC4* promoter" *Plant Mol. Bio.* 43(1):11-21.

Genbank Accession No. AB005879. *Nicotania tabacum* mRNA for BYJ6, Feb. 5, 1999, 2pp.

Genbank Accession No. AC002131. *Arabidopsis thaliana* chromosome 1 BAC F12F1 sequence, May 28, 1998, 38 pp.

Genbank Accession No. AC006461. *Home sapiens* BAC clone RP11-343N14 from 2, Mar. 1, 2002, 65 pp.

Genbank Accession No. ACO21028. *Homo sapiens* clone RP11-137H2 from 10, 44 pp., Oct. 15, 2002.

Genbank Accession No. ACO24028. *Homo sapiens* BAC clone RP11-151M24 from 7, Nov. 7, 2001, 68 pp.

Genbank Accession No. AC069205. *Homo sapiens* BAC clone RP11-735P12 from 2, Jan. 9, 2002, 46 pp.

Genbank Accession No. AC079141. *Homo sapiens* BAC clone RP11-502A23 from 4, Nov. 7, 2001, 43 pp.

Genbank Accession No. AC097498. *Homo sapiens* BAC clone RP11-326N15 from 4, Mar. 1, 2002, 51pp.

Genbank Accession No. AC105416. *Homo sapiens* BAC clone RP11-310A13 from 4, Jun. 12, 2002, 47 pp.

Genbank Accession No. AC108146. *Homo sapiens* BAC clone RP11-437H3 from 2, Mar. 9, 2002, 32 pp.

Genbank Accession No. AC115109. *Homo sapiens* BAC clone RP11-78110 from 2, May 29, 2002, 23 pp.

Genbank Accession No. AR164048. Sequence 7 from patent US 6,271,031, Oct. 17, 2001, 1 pp.

Genbank Accession No. AR164050. Sequence 11 from patent US 6,271,031, Oct. 17, 2001, 1pp.

Genbank Accession No. AX344860. Sequence 285 from PCT publication WO0200927, Feb. 1, 2002, 4pp.

Genbank Accession No. U27809. Peanut bud necrosis virus S segment non-structural protein and nucleocapsid protein genes, Jul. 23, 1996, 3 pp.

Hashimoto et al. "Intraspecific Variability of the Tandem Repeats in *Nicotiana* Putrescine N-Methyltransferases" *Plant Molecular Biology* 37:25-37 (1998) (Abstract).

Hermaisteens "The *Agrobacterium tumefaciens* Ti Plasmid as a Host Vector System for Introducing Foreign DNA in Plant Cells" *Nature* 287: 654-656 (1980).

Herrera-Estrella et al., "Chimeric Genes as Dominant Selectable Markers in Plant Cells" *The EMBO Journal* 2(6):987-995 (1993).

Herrera-Estrella et al. "Expression of Chimaeric Genes Transferred into Plant Cells Using a Ti-Plasmid-Derived Vector" *Nature* 303:209-213 (1983).

Hooykaas et al., "The Ti-Plasmid of *Agrobacterium Tumefaciens*: A Natural Genetic Engineer" *TIBS* 10:307-309 (1985).

Horsch et al. "A Simple and General Method for Transferring Genes into Plants" *Science* 227:1229-1231 (1985).

Hsu et al. "Phloem Mobility of Xenobiotics VI. A Phloem-Mobile Pro-Nematocide based on Oxamyl Exhibiting Root-Specific Activation in Transgenic Tobacco" *Pestic. Sci.* 44:9-19 (1995).

Imanishi et al. "Differential Induction by Methyl Jasmonate of Genes Encoding Ornithine Decarboxylase and Other Enzymes Involved in Nicotine Biosynthesis in Tobacco Cell Cultures" *Plant Molecular Biology* 38:1101-1111 (1998).

Johnson et al. (2001) "Regulation of DNA binding and trans-activation by a xenobiotic stress-activated plant transcription factor" *J. Biol. Chem.* 276(1):172-178.

Keller et al. "Specific Expression of Novel Cell Wall Hydroxyproline-Rich Glycoprotein Gene in Lateral Root Initiation" *Genes & Dev.* 3:1639-1646 (1989) (Abstract Only).

Kitamoto et al. "Increased Activity of Nuclear Factor- κb Participates in Cardiovascular Remodeling Induced by Chronic Inhibition of Nitric Oxide Synthesis in Rats" *Circulation* 102:806-812 (2000).

Konopka (2000) "Rev-binding aptamer and CMV promoter act as decoys to inhibit HIV replication" *Gene* 255(2):235-244.

Kubota et al. "Cloning of a Nuclear-Encoded Photosystem 1 Gene, *psaEb*, in *Nicotiana sylvestris* " *Plant Physiol* 108:1297-1298 (1995).

Lee et al. "CRE-Transcription Factor Decoy Oligonucleotide Inhibition of MCF-7 Breast Cancer Cells: Cross-Talk with p53 Signaling Pathway" *Biochemistry* 39:4863-4868 (2000).

Lerner et al. "Cloning and Characterization of Root-Specific Barley Lectin" *Plant Physiology* 91:124-129 (1989).

Lorz et al. "Transformation Studies Using Synthetic DNA Vectors Coding for Antibiotic Resistance" *Plant Tissue Culture* pp. 511-512 (1982).

Maniatis et al. "Regulation of Inducible and Tissue Specific Gene Expression" *Science* 237:1237-1244 (1987).

Mann et al. "Ex-vivo Gene Therapy of Human Vascular Bypass Grafts with E2F Decoy: The PREVENT Single-Centre, Randomised, Controlled Trial" *The Lancet* 354:1493-1498 (Oct. 30, 1999).

Mann et al. "Pressure-Mediated Oligonucleotide Transfection of Rat and Human Cardiovascular Tissues" *Proc. Natl. Acad. Sci USA* 96:6411-6416 (May 1999).

Mischiati et al. "Interaction of the Human NF-κb p52 Transcription Factor with DNA-PNA Hybrids Mimicking the NF- κb Binding Sites of the Human Immunodeficiency Virus Type 1 Promoter" *The Journal of Biological Chemistry* 274(46):33114-33122 (1999).

Morishita et al. (1995) "A gene therapy strategy using a transcription factor decoy of the E2F binding site inhibits smooth muscle proliferation in vivo" *Proc. Natl. Acad. Sci. USA* 92(13):5855-5859.

Morishita et al. "Application of Transcription Factor "Decoy" Strategy as Means of Gene Therapy and Study of Gene Expression in Cardiovascular Disease" *Circ. Res.* 82:1023-1028 (1998).

Morishita et al. "Role of AP-1 Complex in Angiotensin II-Mediated Transforming Growth Factor-β Expression and Growth of Smooth Muscle Cells: Using Decoy Approach Against AP-1 Binding Site" *Biochemical and Biophysical Research Communications* 243:361-367 (1998).

Nastruzzi et al. "Liposomes as Carriers for DNA-PNA Hybrids" *Journal of Controlled Release* 68:237-249 (2000).

GenBank Accession No. D42070 Tobacco psaEb for PSI-E subunit of photosystem I (1995).

GenBank Accession No. X70902 *N. tobacum* T85 for auxin-binding protein (1998).

Park et al. "Dual Blockade of Cyclic AMP Response Element-(CRE) and AP-1-Directed Transcription by CRE-Transcription Factor Decoy Oligonucleotide" *The Journal of Biological Chemistry* 274(3):1573-1580 (Jan. 15, 1999).

Piva et al. "Modulation of Estrogen Receptor Gene Transcription in Breast Cancer Cells by Liposome Delivered Decoy Molecules" *Journal of Steroid Biochemistry and Molecular Biology* 75:121-128 (2000).

Rafty et al. "Novel Negative Regulator Element in the Platelet-Derived Growth Factor B Chain Promoter That Mediates ERK-Dependent Transcriptional Repression" *The Journal of Biological Chemistry* 275(15):11478-11483 (Apr. 14, 2000).

Reichers et al. "Structure and Expression of the Gene Family Encoding Putrescine N-methyltransferase in *Nicotiana tabacum*: New Clues to the Evolutionary Origin of Cultivated Tobacco" *Plant Molecular Biology* 41:387-401 (1999).

Sanford et al. "The Biolistic Process" *Trends in Biotechnology* 6:299-302 (1988).

Satyanarayana et al., "Peanut Bud Necrosis Tospovirus S RNA : Complete Nucleotide Sequence, Genome Organization and Homology to Other Tospoviruses" *Arch. Virol.* 141(1):85-98 (1996) (Abstract Only).

Sharma et al. (1996) "Transcription factor decoy approach to decipher the role of NF-κB in oncogenesis" *Anticancer Res.* 16(1):61.

Siebertz et al. (1989) "*cis*-Analysis of the wound-inducible promoter *wun1* in transgenic tobacco plants and histochemical localization of its expression" *Plant Cell* 1(10):961-968.

Singer et al. "Transcription: The Transfer of DNA Sequence Information to RNA", in *Genes and Genomes*, section 3.2: 134-145, University Science Books, Mill Valley, CA (1991).

Smith et al. "Antisense RNA Inhibition of Polygalacturonase Gene Expression in Transgenic Tomatoes" *Nature* 334: 724-726 (1988).

Takata et al. "Novel *Cis* Element for Tissue-Specific Transcription of Rat Platelet-Derived Growth Factor β-Receptor Gene" *Hypertension* 33(II):298-302 (1999).

The Sanger Centre, "Toward a Complete Human Genome Sequence", *Genome Research* Cold Spring Harbor Laboratory Press, pp. 1097-1108, (1988).

Theologis et al. "Sequence and Analysis of Chromosome 1 of the Plant *Arabidopsis Thaliana*" *Nature* 408:816-820 (2000).

Tomita et al. "Transcription Factor Decoy for NF B Inhibits Cytokine and Adhesion Molecule Expressions in Synovial Cells Derived from Rheumatoid Arthritis" *Rheumatology* 39:749-757 (2000).

Wadgaonkar et al. (1999) "CREB-binding protein is a nuclear integrator of nuclear factor-κB and p53 signaling" *J. Biol. Chem.* 274(4):1879-1882.

Wang et al. (1992) Characterization of *cis*-acting elements regulating transcription from the promoter of a constitutively active rice actin gene. *Mol. Cell Biol.* 12(8):3399-3406.

Wang et al., "Right 25 bp Terminus Sequence of the Nopaline T- DNA is Essential for and Determines Direction of DNA Transfer from Agrobacterium to the Plant Genome" *Cell* 38: 455-462 (1984).

Wang et al. "Targeted Disruption of Stat6 DNA Binding Activity by an Oligonucleotide Decoy Blocks IL-4-Driven $T_H2$ Cell Response" *Blood* 95(4):1249-1257 (Feb. 15, 2000).

Watanabe et al. "Cloning and Expression of Two Genes Encoding Auxin-Binding Proteins From Tobacco" *Plant Molecular Biology* 36:63-74 (1998).

Wu et al. "Inhibition of In Vitro Transcription by Specific Double-Stranded Oligodeoxyribonucleotides" *Gene* 89:203-209 (1990).

Yamamoto "A Tobacco Root-Specific Gene; Characterization and Regulation of its Expression" *J. Cell Biochem.* 13(D) (Suppl.) (1989) (Abstract).

Yamamoto "A Tobacco Root-Specific Gene; Characterization and Regulation of its Transcription" Ph.D. Thesis submitted to the Graduate Faculty of North Carolina State University. Genetics Department (1989).

Yamamoto et al. "Root-Specific Genes from Tobacco and *Arabidopsis* homologous to an Evolutionary Conserved Gene Family of Membrane Channel Proteins" *Nucleic Acids Research* 18:7449 (1990).

Yamamoto et al. (1991) Characterization of *cis*-acting sequences regulating root-specific gene expression in tobacco. *Plant Cell* 3(4):371-382.

Yia-Herttuala et al. "Cardiovascular Gene Therapy" *The Lancet* 355:213-222 (Jan. 15, 2000).

Beck et al, "Nucleotide Sequence and Exact Localization of the Neomycin Phosphotransferase Gene from Transposon Tn 5", Gene, 19: 327-336 (1982).

Bevan & Flavell, "A Chimaeric Antibiotic Resistance Gene as a Selectable Marker for Plant Cell Transformation", Nature, 304: 184-187 (1983).

Chilton et al., "Tailoring the Agrobacterium Ti Plasmid as a Vector for Plant Genetic Engineering", Stadler Symp., 13: 39-53 (1981).

Colbere-Garapin et al., "A New Dominant Hybrid Selective Marker for Higher Eukaryotic Cells", J. Mol. Biol., 150: 1-14 (1981).

Davies and Jimenez, "A New Selective Agent for Eukaryotic Cloning Vectors", Am. J. Trop. Med. Hyg., 29(5): 1089-1092 (1980).

Fraley et al., "Expression of Bacterial Genes in Plant Cells", Proc. Natl. Acad. Sci. USA, 80: 4803-4807 (1983).

Fraley et al.,"Use of a Chimeric Gene to Confer Antibiotic Resistance to Plant Cells", Advances in Gene Technology: Molecular Genetics of Plants and Animals, 20: 211-221 (1983).

Framond et al., "Mini-Ti: A New Vector Strategy for Plant Genetic Engineering", BIO/TECHNOLOGY, 5: 262-269 (1983).

Hermaisteens et al., "The Agrobacterium Tumefaciens Ti Plasmid as a Host Vector System for Introducing Foreign DNA in Plant Cells", Nature, 287: 654-656 (1980).

Herrera-Estrella et al., "Chimeric Genes as Dominant Selectable Markers in Plant Cells", The Embo Journal, 2(6): 987-995 (1993).

Herrera-Estrella et al., "Expression of Chimaeric Genes Transferred into Plant Cells Using a Ti-Plasmid-Derived Vector", Nature, 303: 209-213 (1983).

Hooykaas et al., "The Ti-Plasmid of Agrobacterium Tumefaciens: A Natural Genetic Engineer", TIBS,307- 309 (1985).

Horsch et al., "A Simple-and General Method for Transferring Genes into Plants", Biological Sciences, 227: 1229-1231 (1985).

Lorz et al., "Transformation Studies Using Synthetic DNA Vectors Coding for Antibiotic Resistance", Plant Tissue Culture, 511-512 (1982).

Smith et al., "Antisense RNA Inhibition of Polygalacturonase Gene Expression in Transgenic Tomatoes", Nature, 334: 724-726 (1988).

Wang et al., "Right 25 bp Terminus Sequence of the Nopaline T- DNA is Essential for and Determines Direction of DNA Transfer from Agrobacterium to the Plant Genome", Cell, 38: 455-462 (1984).

Genbank entry U27809. Peanut bud necrosis virus S segment nonstructural protein and nucleocapsid protein genes, Jul. 23, 1996, 3 pp.

The Sanger Centre, "Toward a Complete Human Genome Sequence", Cold Spring Harbor Laboratory Press, 1097-1108, (1988).

Satyanarayana et al., "Peanut Bud Necrosis Tospovirus S RNA : Complete Nucleotide Sequence, Genome Organization and Homology to Other Tospoviruses", Arch. Virol. 141 (1), 85-98 (1996).

Genbank entry AB005879. *Nicotania tabacum* mRNA for BYJ6, Feb. 5, 1999, 2pp.

Genbank entry AC002131. *Arabidopsis thaliana* chromosome 1 BAC F12F1 sequence, May 28,1998, 38 pp.

Genbank entry AC006461. *Homo sapiens* BAC clone RP11-343N14 from 2, Mar. 1, 2002, 65 pp.

Genbank entry AC024028. *Homo sapiens* BAC clone RP11-151M24 from 7, Nov. 7, 2001, 68 pp.

Genbank entry AC069205. *Homo sapiens* BAC clone RP11-735P12 from 2, Jan. 9, 2002, 46 pp.
Genbank entry AC079141. *Homo sapiens* BAC clone RP11-502A23 from 4, Nov. 7, 2001, 43 pp.
Genbank entry AC097498. *Homo sapiens* BAC clone RP11-326N15 from 4, Mar. 1, 2002, 51pp.
Accession No. AC115109.2.1.59356, Ensembl Human Genome Server, Jun. 10, 1997.
Adams et al. "Biogenesis and Chemistry of Alkaloid-Derived N-Nitronsamines" 184th *American Chemical Society National Meeting* abstract #66 (1982).
Adams et al. "On the Pharmacokinetics of Tobacco-Specific N-Nitrosamines in Fischer Rats" *Carcinogenesis* vol. 6, pp. 509-511 (1985).
Adams et al. "Pharmacokinetics of Tobacco-Specific N-Nitrosamines" *World Health Organization International Agency for Research on Cancer Scientific Publications* No. 57, pp. 779-785 (1984).
Adams et al. "Tobacco-Specific N-Nitrosamines in Dry Snuff" *Fd Chem Toxic* 25(3): 245-246 (1987).
Adams et al. "Toxic and Carcinogenic Agents in Undiluted Mainstream Smoke and Sidestream Smoke of Different Types of Cigarettes" *Carcinogenesis* 8(5): 729-731 (1987).
Andersen et al. "Accumulation of 4-(N-Methyl-N-nitrosamino)-1-(3-pyridyl)-1-butanone in Alkaloid Genotypes of Burley Tobacco During Postharvest Processing: Comparisons with N'-Nitrosonornicotine and Probable Nitrosamine Precursors" *Cancer Research* 45: 5287-5293 (1985).
Andersen et al. "Effect of Storage Conditions on Nitrosated, Acylated, and Oxidized Pyridine Alkaloid Derivatives in Smokeless Tobacco Products" *Cancer Research* 49: 5895-5900 (1989).
Andersen et al. "Effects of Air-Curing Environment on Alkaloid-Derived Nitrosamines in Burley Tobacco" *IARC Science Publication* 84: 451-455 (1987).
Andersen et al. "Levels of Alkaloids and Their Derivatives in Air- and Fire-Cured KY 171 Dark Tobacco During Prolonged Storage: Effects of Temperature and Moisture" *Tobacco Science* 34: 50-56 (1990).
Andersen et al. "N'-Acyl and N'-Nitroso Pyridine Alkaloids in Alkaloid Lines of Burley Tobacco During Growth and Air-Curing" *J Agric Food Chem* 37: 44-50 (1989).
Andersen et al. "pH Changes in Smokeless Tobaccos Undergoing Nitrosation" *ACS Symposium Series Nitrosamines and Related N-Nitroso Compounds* Chapter 29 pp. 320-321 (1992).
Andersen et al. "Total Carbonyls and Phenols in Experimental Burley and Bright Tobacco" *J Agric Food Chem* 27(4): 891-895 (1979).
Atawodi et al. "Tobacco-Specific Nitrosamines in Some Nigerian Cigarettes" *Cancer Letters* 97: 1-6 (1995).
Bae et al. "The Nitrosation of Hexetidine and Hexedine: Characterization of the Major Nitrosamine from Common Antimicrobial Agents" *Chem Res Toxicol* 7: 868-876 (1994).
Bandurski et al. "Hormone Biosynthesis and Metabolism: B1. Auxin Biosynthesis and Metabolism" *Plant Hormones* P.J. Davies (ed.) pp. 39-51 (1995).
Bhide et al. "Tobacco-Specific N-Nitrosamines [TSNA] in Green Mature and Processed Tobacco Leaves from India" *Beitrage zur Tabakforschung International* 14(1): 29-32 (1987).
Blaszczyk et al. "Increased Resistance to Oxidative Stress in Transgenic Tobacco Plants Overexpressing Bacterial Serine Acetyltransferase" *The Plant Journal* 20(2): 237-243 (1999).
Brittebo et al. "Metabolism of Tobacco-Specific Nitrosamines by Cultured Rat Nasal Mucosa" *Cancer Research* 43: 4343-4348 (1983).
Brunnemann "Topics related to N-Nitrosamines and Their Precursors" 45th *TCRC* Oct. 20-23, 1991 *Asheville, NC*.
Brunnemann et al. "Analytical Studies on N-Nitrosamines in Tobacco and Tobacco Smoke" *Recent Advances in Tobacco Science* vol. 17 pp. 71-112 (1991).
Brunnemann et al. "Analytical Studies on Tobacco-Specific N-Nitrosamines in Tobacco and Tobacco Smoke" *Critical Reviews in Toxicology* 21(4): 235-240 (1991).
Brunnemann et al. "Assessment of the Carcinogenic N-Nitrosodiethanolamine in Tobacco products and Tobacco Smoke" *Carcinogenesis* 2(11): 1123-1127 (1981).

Brunnemann et al. "Identification and Analysis of a New Tobacco-Specific N-nitrosamine, 4-(methylnitrosamino)-4-(3-pyridyl)-1-butanol" *Carcinogenesis* 8(3): 465-469 (1987).
Brunnemann et al. "Isolation, Identification and Bioassay of the Tobacco-Specific N-Nitrosamine, 4-(Methylnitrosamino)-4-(3-Pyridyl)-1-Butanol" *Seventy-Ninth Annual Meeting of the American Association for Cancer Research* vol. 29, abstract 332 (1988).
Brunnemann et al. "N-Nitrosamines in Chewing Tobacco: An International Comparison" *J Agric Food Chem* 33:1178-1181 (1985).
Brunnemann et al. "N-Nitrosamines: Environmental Occurrence, in Vivo Formation and Metabolism" 183rd *American Chemical Society National Meeting* abstract 34 (1982).
Brunnemann et al. "N-Nitrosamines: Environmental Occurrence, in-Vivo Formation and Metabolism" *J Toxicology—Clinical Toxicology* 19(6&7): 661-688 (1982-83).
Brunnemann et al. "N-Nitrosodiethanolamine in Tobacco and Mainstream and Sidestream Smoke" *World Health Organization Environmental Carcinogens Selected Methods of Analysis* vol. 6 pp. 85-92 (1983).
Brunnemann et al. "Role of Tobacco Stems in the Formation of N-Nitrosamines in Tobacco and Cigarette Mainstream and Sidestream Smoke" *J Agric Food Chem* 31: 1221-1224 (1983).
Burton et al. "Accumulation of Tobacco-Specific Nitrosamines During Curing and Aging of Tobacco" *American Chemical Society Symposium Series: Nitrosamines and Related N-Nitroso Compounds* Chapter 41 pp. 361-362 (1992).
Burton et al. "Changes in Chemical Composition of Burley Tobacco During Senescence and Curing 2. Acylated Pyridine Alkaloids" *J Agric Food Chem* 36: 579-584 (1988).
Burton et al. "Changes in Chemical Composition of Burley Tobacco During Senescence and Curing 3. Tobacco-Specific Nitrosamines" *J Agric Food Chem* 37: 426-430 (1989).
Burton et al. "Changes in Chemical Composition of Tobacco Lamina During Senescence and Curing 1. Plastid Pigments" *J Agric Food Chem* 33; 879-883 (1985).
Burton et al. "Distribution of Tobacco Constituents in Tobacco Leaf Tissue 1. Tobacco-Specific Nitrosamines, Nitrate, Nitrite and Alkaloids" *J Agric Food Chem* 40: 1050-1055 (1992).
Burton et al. "Distribution of Tobacco Constituents in Tobacco Leaf Tissue 1. Tobacco-Specific Nitrosamines, Nitrate, Nitrite and Alkaloids" slides reprint from *J Agric Food Chem* vol. 40 (1992).
Burton et al. "Influence of Temperature and Humidity on the Accumulation of Tobacco-Specific Nitrosamines in Stored Burley Tobacco" *J Agric Food Chem* 37: 1372-1377 (1989).
Burton et al. "Relationship Between Tobacco-Specific Nitrosamines and Nitrite from Different Air-Cured Tobacco Varieties" *J Agric Food Chem* 42: 2007-2011 (1994).
Burton et al. "The Effects of Harvesting and Curing Procedures on the Composition of the Cured Leaf" *Tobacco Science* vol. 5 pp. 49-53 (1963).
Bush et al. "Origin of Nitrite-Nitrogen for Tobacco-Specific N'-Nitrosamine Formation" *Technologie-Agriculture*, No. 9814, p. 139 (1995).
Carmella et al. "Formation of Hemoglobin Adducts upon Treatment of F344 Rats with the Tobacco-specific Nitrosamines 4-(Methylnitrosamino)-1-(3-pyridyl)-1-butanone and N'-Nitrosonornicotine" *Cancer Research* 47: 2626-2630 (1987).
Carmella et al. "Mass Spectrometric Analysis of Tobacco-Specific Nitrosamine Hemoglobin Adducts in Snuff Dippers, Smokers, and Nonsmokers" *Cancer Research* 50: 5438-5445 (1990).
Carmella et al. "Metabolites of the Tobacco-Specific Nitrosamine 4-(Methylnitrosamino)-1-(3-pyridyl)-1-butanone in Smokers' Urine" *Cancer Research* 53: 721-724 (1993).
Carter et al. "Tobacco Nectarin V Is a Flavin-Containing Berberine Bridge Enzyme-Like Protein with Glucose Oxidase Activity" *Plant Physiology* 134: 460-469 (2004).
Castonguay et al. "Carcinogenicity, Metabolism and DNA Binding of the Tobacco Specific Nitrosamine, 4-(Methylnitrosamino)-1-(3-Pyridyl)-1-Butanone (NNK)" *Seventy-Second Annual Meeting of the American Association for Cancer Research* abstract 297 (1981).

Castonguay et al. "Metabolism of Tobacco-Specific Nitrosamines in Cultured Human Tissues" *Seventy-Third Annual Meeting of the American Association for Cancer Research* vol. 23, abstract 333 (1982).

Chamberlain et al. "Chemical Composition of Nonsmoking Tobacco Products" *J Agric Food Chem* 36: 48-50 (1988).

Chamberlain et al. "Curing Effects on Contents of Tobacco Specific Nitrosamines in Bright and Burley Tobaccos" $41^{st}$ TCRC #53 (1987).

Chamberlain et al. "Effects of Curing and Fertilization on Nitrosamine Formation in Bright and Burley Tobacco" *Beitrage zur Tabakforschung International* 15(2): 87-92 (1992).

Chamberlain et al. "Studies on the Reduction of Nitrosamines in Tobacco" *Tobacco Science* 38-39: 81-82 (1985).

Chaplin et al. "Catalog of the Tobacco Introductions in the U.S. Department of Agriculture's Tobacco Germplasm Collection (*Nicotiana tabacum* )" *U.S. Department of Agriculture, Agricultural Reviews and Manuals* (1982).

Chintapakorn et al. "Antisense-mediated Down-regulation of Putrescine N-methyltransferase Activity in Transgenic *Nicotiana tabacum* L. Can Lead to Elevated Levels of Anatabine at the Expense of Nicotine" *Plant Molecular Biology* 53: 87-105 (2003).

Creelman et al. "Involvement of a Lipoxygenase-Like Enzyme in Abscisic Acid Biosynthesis" *Plant Physiology* 99: 1258-1260 (1992).

Dewick "Alkaloids" *Medicinal Natural Products: A Biosynthetic Approach* Chapter 6, pp. 27-374, John Wiley & Sons (1997).

Djordjevic et al. "Accumulation and Distribution of Acylated Nornicotine Derivatives in Flue-Cured Tobacco Alkaloid isolines" *J Agric Food Chem* 38: 347-350 (1990).

Djordjevic et al. "Assessment of Major Carcinogens and Alkaloids in the Tobacco and Mainstream Smoke of USSR Cigarettes" *Int J Cancer* 47: 348-351 (1991).

Djordjevic et al. "The Need for Regulation of Carcinogenic N-Nitrosamines in Oral Snuff" *Fd Chem Toxic* 31(7): 497-501 (1993).

Djordjevic et al. "Tobacco-Specific Nitrosamine Accumulation and Distribution in Flue-Cured Tobacco Alkaloid Isolines" *J Agric Food Chem* 37: 752-756 (1989).

Djordjevic "Tobacco-Specific nitrosamine Accumulation in Different Genotypes of Burley Tobacco at Different Stages of Growth and Air-Curing" $41^{st}$ *Tobacco Chemists'Research Conference* 36 pages (1987).

Doerr-O'Rourke et al. "Effect of Phenethyl Isothiocyanate on the Metabolism of the Tobacco-Specific Nitrosamine 4-(methylnitrosamino)-1-(3-pyridyl)-1-butanone by Cultured Rat Lung Tissue" *Carcinogenesis* 12(6): 1029-1034 (1991).

Elomaa et al. "Transformation of Antisense Constructs of the Chalcone Synthase Gene Superfamily into *Gerbera hybrida*: Differential Effect on the Expression of Family members" *Molecular Breeding* 2:41-50 (1996).

Engelberth et al. "Ion Channel-Forming Alamethicin is a Potent Elicitor of Volatile Biosynthesis and Tendril Coiling. Cross Talk Between Jasmonate and Salicylate Signaling in Lima Bean" *Plant Physiology* 125: 369-377 (2001).

Fischer et al. "Improved Method for the Determination of Tobacco-Specific Nitrosamines (TSNA) in Tobacco Smoke" *Beitrage zur Tabakforschung International* 14(3): 145-153 (1989).

Fischer et al. "Influence of Smoking Parameters on the Delivery of Tobacco-Specific Nitrosamines in Cigarette Smoke—A Contribution to Relative Risk Evaluation" *Carcinogenesis* 10(6): 1059-1066 (1989).

Fischer et al. "Investigations on the Origin of Tobacco-Specific Nitrosamines in Mainstream Smoke of Cigarettes" *Carcinogenesis* 11(5): 723-730 (1990).

Fischer et al. "No Pyrosynthesis of N'-Nitrosonornicotine (NNN) and 4-(Methylnitrosamino)-1-(3- Pyridyl)-1-butanone (NNK) from Nicotine" *Effects of Nicotine on Biological Systems: Advances in Pharmacological Sciences* pp. 103-107 1991.

Fischer et al. "Preformed Tobacco-Specific Nitrosamines in Tobacco—Role of Nitrate and Influence of Tobacco Type" *Carcinogenesis* 10(8): 1511-1517 (1989).

Fischer et al. "Tobacco-Specific Nitrosamines in Canadian Cigarettes" *J Cancer Res Clin Oncol* 116: 563-568 (1990).

Fischer et-al. "Tobacco-Specific Nitrosamines in Commercial Cigarettes: Possibilities for Reducing Exposure" *Relevance to Human Cancer of N-Nitroso Compounds, Tobacco Smoke and Mycotoxins* pp. 489-492 (1991).

Fischer et al. "Tobacco-Specific Nitrosamines in European and USA Cigarettes" *Archiv fur Geschwulstforschung* 60: 169-177 (1990).

Fischer et al. "Tobacco-Specific Nitrosamines in Mainstream Smoke of West German Cigarettes—Tar Alone is Not a Sufficient Index for the Carcinogenic Potential of Cigarette Smoke" *Carcinogenesis* 10(1): 169-173 (1989).

Foiles et al. "Mass Spectrometric Analysis of Tobacco-Specific Nitrosamine-DNA Adducts in Smokers and Nonsmokers" *Chem Res Toxicol* 4: 364-368 (1991).

Fung et al. "Spray Damage and Residue Levels in Tobacco Treated with Various Concentrations of 2, 4-D at Different Stages of Growth" *Australian Journal of Experimental Agriculture and Animal Husbandry* 13: 328-338 (1973).

Gondwe et al. "Screening Tobacco Types, Cultivars and Curing Methods for Low Nitrosamine Tobacco Production in Malawi" *Agricultural Research and Extension Trust 1998 Coresta Congress at Yokohama, Japan* 7 pages.

Hecht et al. "Cyclic and Tobacco-Specific Nitrosamines: Metabolism and Macromolecular Adduct Formation" *Abstracts of Papers: $204^{th}$ American Chemical Society Meeting* abstract 68 (1992).

Hecht et al. "Endogenous Nitrosation of Tobacco Alkaloids in Rats" *Abstracts of Papers: $212^{th}$ American Chemical Society Meeting* abstract 64 (1996).

Hecht et al. "Evidence for 4-(3-pyridyl)-4-oxobutylation of DNA in F344 Rats Treated with the Tobacco-Specific Nitrosamines 4-(methylnitrosamino)-1-(3-pyridyl)-1-butanone and N'-nitrosonornicotine" *Carcinogenesis* 9(1): 161-165 (1988).

Hecht et al. "HPLC-TEA of Tobacco-Specific Nitrosamines" *World Health Organization: Environmental Carcinogens Selected Methods of Analysis* H. Egan (ed) 6: 429-436 (1983).

Hecht et al. "Induction of Oral Cavity Tumors in F344 Rats by Tobacco-Specific Nitrosamines and Snuff" *Cancer Research* 46: 4162-4166 (1986).

Hecht et al. "Metabolism of the Tobacco-Specific Nitrosamine 4-(methylnitrosamino)-1-(3-pyridyl)-1-butanone in the Patas Monkey: Pharmacokinetics and Characterization of Glucuronide Metabolites" *Carcinogenesis* 14(2); 229-236 (1993).

Hecht et al. "Reaction of Nicotine and Sodium Nitrite: Formation of Nitrosamines and Fragmentation of the Pyrrolidine Ring" *J Organic Chemistry* 43(1): 72-76 (1978).

Hecht et al. "Recent Studies on the Metabolic Activation of Tobacco-Specific Nitrosamines" *Abstracts of Papers Part 1: $217^{th}$ American Chemical Society National Meeting* abstract 012 (1999).

Hecht et al. "The Metabolism of Cyclic Nitrosamines" N-*Nitroso Compounds ACS Symposium Series* 174 pp. 49-75 (1981).

Hecht et al. "The Relevance of Tobacco-Specific Nitrosamines to Human Cancer" *Cancer Surveys* 8(2): 273-294 (1989).

Hecht et al. "Tobacco-Specific Nitrosamine Adducts: Studies in Laboratory Animals and Humans " *Environmental Health Perspectives* 99: 57-63 (1993).

Hecht et al. "Tobacco-Specific Nitrosamines in Tobacco and Tobacco Smoke" *World Health Organization: Environmental Carcinogens Selected Methods of Analysis* H. Egan (ed) 6: 93-101 (1983).

Hecht et al. "Tobacco-specific Nitrosamines, an Important Group of Carcinogens in Tobacco and Tobacco Smoke" *Carcinogenesis* 9(6): 875-884 (1988).

Hecht et al. "Tobacco-Specific Nitrosamines: Formation from Nicotine in Vitro and During Tobacco Curing and Carcinogenicity in Strain A Mice" *J Natl Cancer Inst* 60(4): 819-824 (1978).

Hecht et al. "Tobacco-Specific Nitrosamines: Occurrence, Formation, Carcinogenicity and Metabolism" *Accounts of Chemical Research* 12: 92-98 (1979).

Hecht et al. "2'-Hydroxylation of Nicotine by Cytochrome P450 2A6 and Human Liver Microsomes: Formation of a Lung Carcinogen Precursor" *PNAS* 97(23): 12493-12497 (2000).

Hecht et al. "A Study of Tobacco Carcinogenesis XLII. Bioassay in A/J Mice of Some Structural Analogues of Tobacco-Specific Nitrosamines" *Cancer Letters* 42: 141-145 (1988).

Hecht et al. "Biochemistry, Biology and Carcinogenicity of Tobacco-Specific N-Nitrosamines" *Chemical Research in Toxicology* 11(6): 560-603 (1998).

Hecht et al. "Biomarkers for Human Uptake and Metabolic Activation of Tobacco-Specific Nitrosamines" *Cancer Research (supplemental)* 54: 1912s-1917s (1994).

Hecht et al. "Chemical Studies on Tobacco Smoke. XXXIII. N'-Nitrosonornicotine in Tobacco: Analysis of Possible Contributing Factors and Biologic Implications" *Journal of the National Cancer Institute* 54(5): 1237-1244 (1974).

Hecht et al. "Comparative Carcinogenicity in F344 Rats of the Tobacco-specific Nitrosamines, N'-Nitrosonornicotine and 4-(N-Methyl-N-nitrosamino)-1-(3-pyridyl)-1-butanone" *Cancer Research* 40: 298302 (1980).

Hecht et al. "Comparative Carcinogenicity of o-Toluidine Hydrochloride and O-Nitrosotoluene in F-344 Rats" *Cancer Letters* 16: 103-108 (1982).

Hecht et al. "DNA Adduct Formation from Tobacco-Specific N-Nitrosamines" *Mutation Research* 424: 127-142 (1999).

Heeschen et al. "Nicotine Stimulates Angiogenesis and Promotes Tumor Growth and Atherosclerosis" *Nature Medicine* 7(7): 833-839 (2001).

Hoffmann et al. "Assessment of Tobacco-Specific N-Nitrosamines in Tobacco Products" *Cancer Research* 39: 2505-2509 (1979).

Hoffmann et al. "Carcinogenic Tobacco-specific *N*-Nitrosamines in Snuff and in the Saliva of Snuff Dippers" *Cancer Research* 41: 4305-4308 (1981).

Hoffmann et al. "Chemical Studies on Tobacco Smoke. XXVI. On the Isolation and Identification of Volatile and Non-Volatile *N*-Nitrosamines and Hydrazines in Cigarette Smoke" *Int Agency Res Cancer Publ* 9: 159-165 (1974).

Hoffmann et al. "Formation and Analysis of N-Nitrosamines in Tobacco Products and Their Endogenous Formation in Consumers" *N-Nitroso Compounds: Occurrence, Biological Effects and Relevance to Human Cancer*, World Health Organization, Proceedings of the VIIIth International Symposium on N-Nitroso Compounds, pp. 743-762 (1983).

Hoffmann et al. "Formation of Tobacco-Specific Nitrosamines: Carcinogenicity and Role of Dietary Fat in Their Carcinogenicity" *Nitrosamines and Related N-Nitroso Compounds* chapter 21, pp. 267-278 (1994).

Hoffmann et al. "Formation of Tobacco-Specific N-Nitrosamines, Their Carcinogenicity and the Role of Dietary Fat in their Carcinogenicity" Abstracts of Papers: 204th American Chemical Society National Meeting abstract 119 (1992).

Hoffmann et al. "Formation, Occurrence and Carcinogenicity of N-Nitrosamines in Tobacco Products" *Abstracts of Papers: 181st American Chemical Society National Meeting* abstract 59 (1981).

Hoffmann et al. "GC-TEA of Volatile Nitrosamines from Tobacco Products" *World Health Organization Environmental Carcinogens Selected Methods of Analysis* vol. 6, pp. 363-366 (1983).

Hoffmann et al. "Introduction: Tobacco-Specific N-Nitrosamines (TSNA)" *Critical Reviews in Toxicology* 21(4) (1991).

Hoffmann et al. "Nicotine: A Precursor for Carcinogens" *Cancer Letters* 26: 67-75 (1985).

Hoffmann et al. "Nicotine-Derived N-Nitrosamines (TSNA) and Their Relevance in Tobacco Carcinogenesis" *Critical Reviews in Toxicology* 21(4): 305-311 (1991).

Hoffmann et al. "Nicotine-Derived N-Nitrosamines and Tobacco-Related cancer: Current Status and Future Directions" *Cancer Research* 45: 935-944 (1985).

Hoffmann et al. "On the Endogenous Formation of N-Nitrosamines in Cigarette Smokers" *Seventy-Fourth Annual Meeting of the American Association for Cancer Research* vol. 24, abstract 241 (1983).

Hoffmann et al. "Origin in Tobacco Smoke of N'-Nitrosonornictoine, a Tobacco-Specific Carcinogen: *Brief Communication*" *J Natl Cancer Inst* 58(6): 1841-1844 (1977).

Hoffmann et al. "The Role of Volatile and Non volatile *N*-Nitrosamines in Tobacco Carcinogenesis" pp. *Banbury Report, vol. 3: A Safe Cigarette* Gori and Bock, editors. Cold Spring Harbor Laboratory. pp. 113-127 (1980).

Hoffmann et al. "Tobacco and Tobacco Smoke (Volatile and Tobacco-Specific Nitrosamines): General Aspects" *World Health Organization Environmental Carcinogens Selected Methods of Analysis* vol. 6, pp. 63-67 (1983).

Hoffmann et al. "Tobacco Specific *N*-Nitrosamines: Occurrence and Bioassays" *N-Nitroso Compounds: Occurrence and Biological Effects* World Health Organization, Proceedings of the VIIth International Symposium on N-Nitroso Compounds pp. 309-318 (1981).

Hoffmann et al. "Tobacco-Specific *N*-Nitrosamines and *Areca*-Derived *N*-Nitrosamines: Chemistry, Biochemistry, Carcinogenicity, and Relevance to Humans" *Journal of Toxicology and Environmental Health* 41: 1-52 (1994).

Hoffmann et al. "Volatile Nitrosamines in Tobacco and Mainstream and Sidestream Smoke and Indoor Environments" *World Health Organization Environmental Carcinogens Selected Methods of Analysis* vol. 6, pp. 69-83 (1983).

Johnson et al. "*N*-Nitrosamines in Smoke Condensate from Several Varieties of Tobacco" *Journal of the National Cancer Institute* 48(6): 1845-1847 (1972).

Kahl et al. "Herbivore-induced Ethylene Suppresses a Direct Defense but Not a Putative Indirect Defense Against an Adapted Herbivore" *Planta* 210: 336-342 (2000).

Kolomiets et al. "Lipoxygenase is Involved in the Control of Potato Tuber Development" *The Plant Cell* 13: 613-626 (2001).

Kumar et al. "Tobacco-Specific *N*-Nitrosamines in Tobacco and Mainstream Smoke of Indian Cigarettes" *Fd Chem Toxic* 29(6): 405-407 (1991).

Larsson et al. "Polycyclic Aromatic Hydrocarbons and Volatile N-Nitrosamines in Some Dried Agricultural Products" *Swedish J Agric Res* 20(2): 49-56 (1990).

Liszewska et al. "Modification of Non-Protein Thiols Contents in Transgenic Tobacco Plants Producing Bacterial Enzymes of Cysteine Biosynthesis Pathway" *Acta Biochimica Polonica* 48(3): 647-656 (2001).

MacKown et al. "Tobacco-Specific *N*-Nitrosamines: Effect of Burley Alkaloid Isolines and Nitrogen Fertility Management" *J Agric Food Chem* 32: 1269-1272 (1984).

MacKown et al. "Tobacco-Specific *N*-Nitrosamines: Formation During Processing of Midrib and Lamina Fines" *J Agric Food Chem* 36: 1031-1035 (1988).

McCoy et al. "Influence of Chronic Ethanol Consumption on the Metabolism and Carcinogenicity of Tobacco-Related Nitrosamines" *World Health Organization N-Nitroso compounds: Occurrence and Biological Effects* Proceedings of the VIIth International Symposium on N-Nitroso Compounds in Tokyo pp. 635-642 (1981).

Melikian et al. "Volatile Nitrosamines: Analysis in Breast Fluid and Blood of Non-Lactating Women" *Fd Cosmet Toxicol* 19: 757-759 (1981).

Mingwu et al. "Effect of Maleic Hydrazide Application on Accumulation of Tobacco-Specific Nitrosamines in Air-Cured Burley Tobacco" *J Agric Food Chem* 42: 2912-2916 (1994).

Mirvish et al. "Ascorbate-Nitrite Reaction: Possible Means of Blocking the Formation of Carcinogenic *N*-Nitroso Compounds" *Science* 177: 65-68 (1972).

Mitacek et al. "Volatile Nitrosamines and Tobacco-Specific Nitrosamines in the Smoke of Thai Cigarettes: A Risk Factor for Lung Cancer and a Suspected Risk Factor for Liver Cancer in Thailand" *Carcinogenesis* 20(1): 133-137 (1999).

Nair et al. "Carcinogenic Tobacco-Specific Nitrosamines in Indian Tobacco Products" *Chem Toxic* 27(11): 751-753 (1989).

Osterdahl et al. "*N*-Nitrosamines in Snuff and Chewing Tobacco on the Swedish Market in 1983" *Food Additives and Contaminants* 1(4): 299-305 (1984).

Osterdahl et al. "Volatile *N*-Nitrosamines in Snuff and Chewing Tobacco on the Swedish Market" *Fd Chem Toxic* 21(6): 759-762 (1983).

Peele et al. "Formation of Tobacco Specific Nitrosamines in Flue-Cured Tobacco" *Rec Adv Tobacco Sci* 27:3-12 (2001).

Perini "Experimental Cigarette Tobacco Column Tobacco Specific Nitrosamine (TSNA) Concentrations: A Comparison Among Single Blend Component Cigarettes and the Number 1580 Control Cigarette" Memo (1989).

Peterson et al. "Formation of NADP (H) Analogs of Tobacco-Specific Nitrosamines in Rat Liver and Pancreatic Microsomes" *Chem Res Toxicol* 7: 599-608 (1994).

Peterson et al. "Quantitation of Microsomal α-Hydroxylation of the Tobacco-specific Nitrosamine, 4- (Methylnitrosamino)-1-(3-pyridyl)-1-butanone" *Cancer Research* 51: 5495-5500 (1991).

Preston et al. "*Tobacco mosaic* Virus Inoculation Inhibits Wound-Induced Jasmonic Acid-Mediated Responses Within But Not Between Plants" *Planta* 209: 87-95 (1999).

Preston-Martin "Evaluation of the Evidence That Tobacco-Specific Nitrosamines (TSNA) Cause Cancer in Humans" *Toxicology* 21(4): 295-298 (1991).

Prokopczyk et al. "Significance of Nitrosamines in Betel Quid Carcinogenesis" *ACS Symposium Series 553, 204th National Meeting of the American Chemical Society* chapter 43, Jan. 31, 1994.

Prokopczyk et al. "Supercritical Fluid Extraction in the Determination of Tobacco-Specific *N*-Nitrosamines in Smokeless Tobacco" *Chem Res Toxicol* 5: 336-340 (1992).

Reed Characterization of the A/B Regulon in Tobacco (*Nicotiana tabacum* ) Thesis, Virginia Polytechnic Institute and State University (2003).

Renaud et al. "Tobacco-Specific Nitrosamines 940400-940600" *Research and Development, Neuchatel—Quarterly Report* 15 pages (1994).

Rivenson et al. "A Study of Tobacco Carcinogenesis XLIV. Bioassay in A/J Mice of Some *N*-Nitrosamines" *Cancer Letters* 47: 111-114 (1989).

Rivenson et al. "Carcinogenicity of Tobacco-Specific N-Nitrosamines (TSNA): the Role of the Vascular Network in the Selection of Target Organs" *Toxicology* 21(4): 255-264 (1991).

Rivenson et al. "Induction of Lung and Exocrine Pancreas Tumors in F344 Rats by Tobacco-specific and *Areca*-derived *N*-Nitrosamines" *Cancer Research* 48: 6912-6917 (1988).

Rivenson et al. "Observations on Lung Tumors Arising from Metaplastic Squamous Epithelium in Rats Treated Chronically With the Tobacco-Specific Nitrosamines, 4-(Methylnitrosamino)-1-(3-PyridyI)-1- Butanone (NNK)" *Proceedings of the Seventy-Ninth Annual Meeting of the American Association for Cancer Research* vol. 29 Abstract 342 (1988).

Rivenson et al. "Pathogenetic Considerations on Nasal Cavity Tumors Induced by Tobacco Specific Nitrosamines (TSNA) in Rats" *European Journal of Cancer & Clinical Oncology* Abstract pp. 1312 (1983).

Ruhl et al. "Chemical Studies on Tobacco Smoke LXVI. Comparative Assessment of Volatile and Tobacco-Specific N-Nitrosamines in the Smoke of Selected Cigarettes from the U.S.A., West Germany, and France." *Journal of Analytical Toxicology* 4: 255-259 (1980).

Sachan "Identification of Signaling Factors Involved in the Regulation of Alkaloid Metabolism in *N. Tabacum*" Dissertation, University of Kentucky (2004).

Saunders "Effect of Regenerated Roots and Shoots on Nicotine Production in Tobacco Tissue Culture" *Drug Information Journal* 32:609-617 (1998).

Saunders et al. "Nicotine Biosynthetic Enzyme Activities in *Nicotiana tabacum* L. Genotypes with Different Alkaloid Levels" *Plant Physiol* 64: 236-240 (1979).

Schaller et al. "Enzymes of the Biosynthesis of Octadecanoid-Derived Signaling Molecules" *Journal of Experimental Botany* 52(354): 11-23 (2001).

Schmeltz et al. "Nitrogen-Containing Compounds in Tobacco and Tobacco Smoke" *Chemical Reviews* 77(3): 295-311 (1977).

Schweizer et al. "Jasmonate-Inducible Genes Are Activated in Rice by Pathogen Attack Without a Concomitant Increase in Endogenous Jasmonic Acid Levels" *Plant Physiology* 114: 79-88 (1997).

Shoji et al. "Expression Patterns of Two Tobacco Isoflavone Reductase-Like Genes and Their Possible Roles in Secondary Metabolism in Tobacco" *Plant Molecular Biology* 50: 427-440 (2002).

Shoji et al. "Jasmonate Induction of Putrescine *N*-Methyltransferase Genes in the Root of *Nicotiana sylvestris* " *Plant Cell Physiology* 41(7): 931-839 (2000).

Sircar et al. "Soybean Lipoxygenase Inhibition by Nonsteroidal Antiinflammatory Drugs" *Prostaglandins* 25(3): 939-396 (1983).

Sitbon et al. "Expression of Auxin-Inducible Genes in Relation to Endogenous Indoleacetic Acid (IAA) Levels in Wild-Type and IAA-Overproducing Transgenic Tobacco Plants" *Physiologia Plantarum* 98: 677-684 (1996).

Sitbon et al. "Transgenic Tobacco Plants Coexpressing the *Agrobacterium tumefaciens* iaaM and iaaH Genes Display Altered growth and Indoleacetic Acid Metabolism" *Plant Physiology* 99: 1062-1069 (1992).

Spiegelbalder et al. "A Method for the Determination of Tobacco-specific Nitrosamines (TSNA), Nitrate and Nitrite in tobacco Leaves and Processed Tobacco" *Beitrage zur Tabakforschung International* 14(3): 135-144 (1989).

Spiegelhalder et al. "Tobacco-Specific Nitrosamines" *European Journal of Cancer Prevention* 5(suppl. 1): 33-38 (1996).

Splegelhalder et al. "Formation of Tobacco-Specific Nitrosamines" *Critical Reviews in Toxicology* 20(64): 241 (1991).

Staswick et al. "C2. Jasmonates, Salicylic Acid and Brassinolides. C2a. Jasmonate Activity in Plants." *Plant Hormones: Physiology, Biochemistry and Molecular Biology* pp. 179-187, Davies, ed. Kluwer Academic Publishers (1995).

Stedman et al. "The Chemical Composition of Tobacco and Tobacco Smoke" *Chemical Reviews* 68: 153-207 (1968).

Thornburg et al. "Wounding *Nicotiana tabacum* Leaves Causes a Decline in Endogenous Indole-3-Acetic Acid" *Plant Physiol* 96: 802-805 (1991).

Tricker et al. "The Occurrence of *N*-Nitro Compounds in Zarda Tobacco" *Cancer Letters* 42: 113-118 (1988).

Tricker et al. "The Occurrence of Tobacco-Specific Nitrosamines in Oral Tobacco Products and Their Potential Formation Under Simulated Gastric Conditions" *Fd Chem Toxic* 26(10): 861-865 (1988).

Trushin et al. "Stereoselective Metabolism of Nicotine and Tobacco-Specific *N*-Nitrosamines to 4-Hydroxy-4-(3-pyridyl) butanoic Acid in Rats" *Chem Res Toxicol* 12: 164-171 (1999).

Tso "Organic Metabolism—Alkaloids" *Production, Physiology, and Biochemistry of Tobacco Plant* pp. 467-486 IDEALS, Inc. (1990).

Tso "The Loci of Alkaloid Formation" *Physiology and Biochemistry of Tobacco Plants* pp. 233-235, Dowden, Hutchinson & Ross, Inc. (1972).

Uknes et al. "Acquired Resistance in Arabidopsis" *The Plant Cell* 4: 645-656 (1992).

Upadhaya et al. "Preparation of Pyridine-*N*-glucuronides of Tobacco-Specific Nitrosamines" *Chem Res Toxicol* 14: 555-561 (2001).

Wagner et al. "The Pyridine-Nucleotide Cycle in Tobacco Enzyme Activities for the De-Novo Synthesis of NAD" *Planta* 165: 532-537 (1985).

Walling et al. "The Myriad Plant Responses to Herbivores" *J Plant Growth Regul* 19: 195-216 (2000).

Waterhouse et al. "Virus Resistance and Gene Silencing: Killing the Messenger" *Abstract Trends plant Sci* 4(11): 452-457 (1999).

Wawrzynska et al. "Using a Suppression Subtractive Library-Based Approach to Identify Tobacco Genes Required in Response to Short-Term Sulphur Deficit" *Journal of Experimental Botany* 56(416): 1575-1590 (2005).

Wenke et al. "A Study of Betel Quid Carcinogenesis. II. Formation of *N*-Nitrosamines During Betel Quid Chewing" N-*Nitroso Compounds: Occurrence, Biological Effects and Relevance to Human Cancer* World Health Organization International Agency for Research on Cancer, IARC Scientific Publications No. 57, pp. 859-866 (1984).

VViernik et al. "Effect of Air-Curing on the Chemical Composition of Tobacco" *Svenska Tobaks AB, Department Reserca, Recent Advances in Tobacco Science* 21:39-80 (1995).

Winz et al. "Molecular Interactions Between the Specialist Herbivore *Manduca Sexta* (*Lepidoptera Sphingidae*) and its Natural Host *Nicotiana attenuata*. IV. Insect-Induced Ethylene Reduces jasmonate-Induced Nicotine Accumulation by Regulating Putrescine *N*-Methyltransferase Transcipts" *Plant Physiology* 125: 2189-2202 (2001).

Wolbang et al. "Auxin Promotes Gibberellin Biosynthesis in Decapitated Tobacco Plants" *Planta* 214: 153-157 (2001).

Zaridze et al. "The Effect of Nass Use and Smoking on the Risk of Oral Leukoplakia" *Cancer Detection and Prevention* 9: 435-440 (1986).

Genbank entry AC105416. *Homo sapiens* BAC clone RP11-310A13 from 4, Jun. 12, 2002, 47 pp.

Genbank entry AC108146. *Homo sapiens* BAC clone RP11-437H3 from 2, Mar. 9, 2002, 32 pp.

Genbank entry AC115109. *Homo sapiens* BAC clone RP11-78110 from 2, May 29, 2002, 23 pp.

Genbank entry AR164048. Sequence 7 from patent US 6,271,031, Oct. 17, 2001, 1 pp.

Genbank entry AR164050. Sequence 11 from patent US 6,271,031, Oct. 17, 2001, 1pp.

Genbank entry AX344860. Sequence 285 from patent US W00200927, Feb. 1, 2002, 4pp.

Imanishi et al., "Differential Induction by Methyl Jasmonate of Genes Encoding Ornithine Decarboxylase and Other Enzymes Involved in Nicotine Biosynthesis in Tobacco Cell Cultures", Plant Molecular Biology, 38: 1101-1111 (1998).

Theologis et al., "Sequence and Analysis of Chromosome 1 of the Plant *Arabidopsis thaliana*", Nature, 408: 816-820 (2000).

Hamill et al. "Over-Expressing a Yeast Ornithine Decarboxylase Gene in Transgenic Roots of *Nicotiana rustica* can lead to Enhanced Nicotine Accumulation," *Plant Molecular Biology* 15: 27-38 (1990).

Database EMBL Online! EBI; clone TAP0198, Mar. 5, 1996, XP002285509, 2 pages.

Holmberg et al. "Transgenic Tobacco Expressing Vitreoscilla Hemoglobin Exhibits Enhanced Growth and Altered Metabolite Production" *Nature Biotechnology* 15:244-247 (1997).

\* cited by examiner

```
caaaaactat tttccacaaa attcatttca caaccccccc aaaaaaaaac cATGTTTAGA   60
GCTATTCCTT TCACTGCTAC AGTGCATCCT TATGCAATTA CAGCTCCAAG GTTGGTGGTG  120
AAAATGTCAG CAATAGCCAC CAAGAATACA AGAGTGGAGT CATTAGAGGT GAAACCACCA  180
GCACACCCAA CTTATGATTT AAAGGAAGTT ATGAAACTTG CACTCTCTGA AGATGCTGGG  240
TTTCTAGCAA AGGAAGACGG GATCATAGCA GGAATTGCAC TTGCTGAGAT GATATTCGCG  360
GAAGTTGATC CTTCATTAAA GGTGGAGTGG TATGTAAATG ATGGCGATAA AGTTCATAAA  420
GGCTTGAAAT TTGGCAAAGT ACAAGGAAAC GCTTACAACA TTGTTATAGC TGAGAGGGTT  480
GTTCTCAATT TTATGCAAAG AATGAGTGGA ATAGCTACAC TAACTAAGGA AATGGCAGAT  540
GCTGCACACC CTGCTTACAT CTTGGAGACT AGGAAAACTG CTCCTGGATT ACGTTTGGTG  600
GATAAATGGG CGGTATTGAT CGGTGGGGGG AAGAATCACA GAATGGGCTT ATTTGATATG  660
GTAATGATAA AAGACAATCA CATATCTGCT GCTGGAGGTG TCGGCAAAGC TCTAAAATCT  720
GTGGATCAGT ATTTGGAGCA AAATAAACTT CAAATAGGGG TTGAGGTTGA AACCAGGACA  780
ATTGAAGAAG TACGTGAGGT TCTAGACTAT GCATCTCAAA CAAAGACTTC GTTGACTAGG  840
ATAATGCTGG ACAATATGGT TGTTCCATTA TCTAACGGAG ATATTGATGT ATCCATGCTT  900
AAGGAGGCTG TAGAATTGAT CAATGGGAGG TTTGATACGG AGGCTTCAGG AAATGTTACC  960
CTTGAAACAG TACACAAGAT TGGACAAACT GGTGTTACCT ACATTTCTAG TGGTGCCCTG 1020
ACGCATTCCG TGAAAGCACT TGACATTTCC CTGAAGATCG ATACAGAGCT CGCCCTTGAA 1080
GTTGGAAGGC GTACAAAACG AGCATGAgcg ccattacttc tgctataggg ttggagtaaa 1140
agcagctgaa tagctgaaag gtgcaaataa gaatcatttt actagttgtc aaacaaaaga 1200
tccttcactg tgtaatcaaa caaaaagatg taaattgctg gaatatctca gatggctctt 1260
ttccaacctt attgcttgag ttggtaattt cattatagct ttgttttcat gtttcatgga 1320
atttgttaca atgaaaatac ttgatttata agtttggtgt atgtaaaatt ctgtgttact 1380
tcaaatattt tgagatgtt                                              1399
```

FIGURE 2A

```
MFRAIPFTAT VHPYAITAPR LVVKMSAIAT KNTRVESLEV KPPAHPTYDL   50
KEVMKLALSE DAGNLGDVTC KATIPLDMES DAHFLAKEDG IIAGIALAEM  100
IFAEVDPSLK VEWYVNDGDK VHKGLKFGKV QGNAYNIVIA ERVVLNFMQR  150
MSGIATLTKE MADAAHPAYI LETRKTAPGL RLVDKWAVLI GGGKNHRMGL  200
FDMVMIKDNH ISAAGGVGKA LKSVDQYLEQ NKLQIGVEVE TRTIEEVREV  250
LDYASQTKTS LTRIMLDNMV VPLSNGDIDV SMLKEAVELI NGRFDTEASG  300
NVTLETVHKI GQTGVTYISS GALTHSVKAL DISLKIDTEL ALEVGRRTKR  350
A                                                      351
```

FIGURE 2B

```
N. tabacum       MFRAIPFTATVHPYAITAPRLVVKMSAIATKNTRVESLEVKPPAHPTYDL
R. rubrum        *--------RPNH---------------------PVAALS*F----AI
M. leprae        *--------LSDC---------------------EFDAAR--------
S. typhimurium   *--------PPRR*NPDDR*-----------DALL*RINLDI*A----AV
E. coli          *--------PPRR*NPDTR*-----------DELL*RINLDI*G----AV
H. sapien        *---------------D*EG*ALLLPPVTLAALVDSWLREDC*G------
S. cerevisiae    *---------------PVYE-HLLPVNGAWRQDVTNWLSEDV*S------

N. tabacum       KEVMKLALSEDAGNLGDVTCKATIPLDMESDAHFLAKEDGIIAGIA----
R. rubrum        D*AVRRAL*RA**I*ST****AATRAH*RFV*RQPLLGCA--
M. leprae        -DTIRRHLRYGL*I*TQ**V*AGTVVTGSMVPR*P*VIAGVDVALL
S. typhimurium   AQALREDLGGEVDAGN*I*AQL-L*A*TQAH*TVITR*D*VF----CGKR
E. coli          AQALREDLGGTVDANN*I*A*L-L*ENSR*H*TVITR*N*VF----CGKR
H. sapien        ----------------LNYAALVSGAGP*QAALWAKSP*VL----AGQP
S. cerevisiae    ----------------FDFGGYVVGSDLKEANLYCKQD*ML----CGVP N. tabacum       -LAEMIFAEVDPSLKVEWYVNDGDKVHKGLK------FGKVQGNAYNIVI
R. rubrum        --RSAF-ALLDDTVTFTTPLE**AEIAA*QT------VAE*A*A*RT*LA
M. leprae        VLD*VF-GVDGYRVLY--R*E**ARLQS*QP------LLTVQAA*RGLLT
S. typhimurium   WVE*VFIQLAGDDVRLT*H*D***AI*ANQT------VFELN*PARVLLT
E. coli          WVE*VFIQLAGDDVTII*H*D***VINANQS------LFELE*PSRVLLT
H. sapien        FFDAIFTQL---NCQVS*FLPE*S*LVPVAR------VAEVR*P*HDLLL
S. cerevisiae    FAW*VFNQC---ELQVE*LFKE*SFLEPSKNDSGKIVVAKIT*P*K**LL N. tabacum       AERVVLNFMQRMSGIATLTKEMAD--AAH--PAYILETRKTAPGLRLVDK
R. rubrum        *TA*LGHL*****R*RRFG*AI*HT--R*RLTC**T**GLE*
M. leprae        *TM*VCHM*****V*VAWV*AVRGT--K*KIRD**L**ALQ*
S. typhimurium   GTA*V*TL**VASEVRRYVGLL*GT--QTQL*D**L**TAL*
E. coli          G*PTA***V*TL**VASKVRHYVELLEGT--NTQL*D****L****SAL*
H. sapien        G*ATLARC**SAAAAAVEAARGAGWTGHVAGTF***E*
S. cerevisiae    *TAILSRS**TASHKIISLARSTGYKGTIAGT**RLE*

N. tabacum       WAVLIGGGKNHRMGLFDMVMIKDNHISAAGGVGKALKSVDQYLEQNKLQI
R. rubrum        YRC*S*FD*A*L****AVA*SA**SRAR-AGVGHMVRI
M. leprae        YRV*V*LG*TAL*****VA*V*S*VD**RA*R-AAAPEL-PC
S. typhimurium   Y***C***A***L**T*AFL******I*S*S*RQ*VEKAF-W*HPD-APV
E. coli          Y***C***A***L**S*AFL******I*S*S*RQ*VEKAS-W*HPD-APV
H. sapien        YGL*VAASYD*GGLVML*DVVPP*EK*VRAARQ---AADFAL
S. cerevisiae    YSM*VCDTYD*SS**ML*D***W*T*SITN*V*NARA---VCGFAV
```

FIGURE 3

| | | | |
|---|---|---|---|
| N. tabacum | GVEVETRTIEEVREVLDYASQTKTSLTRIMLDNMVVPLSNGDIDVSMLKE | | |
| R. rubrum | EI****--L*QLA*AVGGAEV-----VL*-----DAPT----*TR | | |
| M. leprae | E****S--L*QLDAM*A-EEPEL-----*L***F--*VWQTQV----AVQ | | |
| S. typhimurium | E****N--LDELDDA*K-*GADI-----*****F-----NTDQ----MR* | | |
| E. coli | E**N--LLD*A*K-*GADI-----*****F-----ETEQ----MR* | | |
| H. sapien | K**CSSLQVQAAE-*GADL-----VL***F------KPEELHPTAT | | |
| S. cerevisiae | KI***CLSED*AT*AIE-*GADV-----*****F------KGDGLK*CAQ | | |
| | | | |
| N. tabacum | AVELI---NGRFDTEASGNVTLETVHKIG-QTGVTYISSGALTHSVKALD | | |
| R. rubrum | DMV---ALV*****G*S*D*IAALA-ESD*V******TT | | |
| M. leprae | RRDIR---APTVLL*SGLSNAAIYA-G*DYLAV***RI | | |
| S. typhimurium | KRV---QARL*V*****AE*LREFA-E*DFVG****R* | | |
| E. coli | KRT---KALL*V*****DK*LREFA-E*DFV******Q* | | |
| H. sapien | *LKAQFPSVA---VEA**GIT*DNLPQF-CGPHIDV**M*M**QA*P*** | | |
| S. cerevisiae | SLKNKWNGKKHFLLEC**GLN*DNLEEYLCD-DIDIY*TSSIHQGTPVI* | | |
| | | | |
| N. tabacum | ISKLIDTELALEVGRRTKRA | % Identity | % Similarity |
| R. rubrum | *G*D*VVA-----PPKAERA | 15.9 | 43.2 |
| M. leprae | *G*DL | 18.3 | 37.3 |
| S. typhimurium | LSMRFC | 18.2 | 34.8 |
| E. coli | LSMRFR | 17.9 | 32.8 |
| H. sapien | F***L---F*K*VAPVP*IH | 16.8 | 31.7 |
| S. cerevisiae | F***LAH | 14.6 | 27.8 |

FIGURE 3 continued

TOBACCO PRODUCTS WITH REDUCED NICOTINE

CROSS REFERENCE TO RELATED APPLICATIONS

This application is a continuation application of, and claims priority to, U.S. application Ser. No. 10/356,076, filed Jan. 31, 2003 and issued as U.S. Pat. No. 7,304,220 on Dec. 4, 2007, which is a continuation application of U.S. application Ser. No. 09/021,286, filed Feb. 10, 1998 and issued as U.S. Pat. No. 6,586,661 on Jul. 1, 2003 and which claims the benefit of U.S. Provisional Application No. 60/049,471, filed Jun. 12, 1997. The entire contents of each of these applications are incorporated by reference herein.

FEDERALLY SPONSORED RESEARCH

This invention was made with Government support under National Science Foundation Grant No. MCB-9206506. The Government has certain rights to this invention.

FIELD OF THE INVENTION

This invention relates to plant quinolate phosphoribosyl transferase (QPRTase) and to DNA encoding this enzyme. In particular, this invention relates to the use of DNA encoding quinolate phosphoribosyl transferase to produce transgenic plants having genetically altered nicotine levels, and the plants so produced.

BACKGROUND OF THE INVENTION

The production of tobacco with decreased levels of nicotine is of interest, given concerns regarding the addictive nature of nicotine. Additionally, tobacco plants with extremely low levels of nicotine production, or no nicotine production, are attractive as recipients for transgenes expressing commercially valuable products such as pharmaceuticals, cosmetic components, or food additives. Various processes have been designed for the removal of nicotine from tobacco. However, most of these processes remove other ingredients from tobacco in addition to nicotine, thereby adversely affecting the tobacco. Classical crop breeding techniques have produced tobacco plants with lower levels of nicotine (approximately 8%) than that found in wild-type tobacco plants. Tobacco plants and tobacco having even further reductions in nicotine content are desirable.

One approach for reducing the level of a biological product is to reduce the amount of a required enzyme in the biosynthetic pathway leading to that product. Where the affected enzyme naturally occurs in a rate-limiting amount (relative to the other enzymes required in the pathway), any reduction in that enzyme's abundance will decrease the production of the end product. If the amount of the enzyme is not normally rate limiting, its presence in a cell must be reduced to rate-limiting levels in order to diminish the pathway's output. Conversely, if the naturally-occurring amount of enzyme is rate limiting, then any increase in the enzyme's activity will result in an increase in the biosynthetic pathway's end product.

Nicotine is formed primarily in the roots of the tobacco plant and is subsequently transported to the leaves, where it is stored (Tso, *Physiology and Biochemistry of Tobacco Plants*, pp. 233-34, Dowden, Hutchinson & Ross, Stroudsburg, Pa. (1972)). An obligatory step in nicotine biosynthesis is the formation of nicotinic acid from quinolinic acid, which step is catalyzed by the enzyme quinoline phosphoribosyl transferase ("QPRTase"). QPRTase appears to be a rate-limiting enzyme in the pathway supplying nicotinic acid for nicotine synthesis in tobacco. See, e.g., Feth et al., "Regulation in Tobacco Callus of Enzyme Activities of the Nicotine Pathway", *Planta,* 168, pp. 402-07 (1986); Wagner et al., "The Regulation of Enzyme Activities of the Nicotine Pathway in Tobacco", *Physiol. Plant.,* 68, pp. 667-72 (1986). The modification of nicotine levels in tobacco plants by antisense regulation of putrescence methyl transferase (PMTase) expression is proposed in U.S. Pat. Nos. 5,369,023 and 5,260,205 to Nakatani and Malik. PCT application WO 94/28142 to Wahad and Malik 30 describes DNA encoding PMT and the use of sense and antisense PMT constructs.

SUMMARY OF THE INVENTION

A first aspect of the present invention is an isolated DNA molecule comprising SEQ ID NO:1; DNA sequences which encode an enzyme having SEQ ID NO:2; DNA sequences which hybridize to such DNA and which encode a quinolate phosphoribosyl transferase enzyme; and DNA sequences which differ from the above DNA due to the degeneracy of the genetic code. A peptide encoded by such DNA is a further aspect of the invention.

A further aspect of the present invention is a DNA construct comprising a promoter operable in a plant cell and a DNA segment encoding a quinolate phosphoribosyl transferase enzyme positioned downstream from the promoter and operatively associated therewith. The DNA encoding the enzyme may be in the antisense or sense direction.

A further aspect of the present invention is a method of making transgenic plant cell having reduced quinolate phosphoribosyl transferase (QPRTase) expression, by providing a plant cell of a type known to express quinolate phosphoribosyl transferase; transforming the plant cell with an exogenous DNA construct comprising a promoter and DNA comprising a portion of a sequence encoding quinolate phosphoribosyl transferase mRNA.

A further aspect of the present invention is a transgenic plant of the species *Nicotiana* having reduced quinolate phosphoribosyl transferase (QPRTase) expression relative to a non-transformed control plant. The cells of such plants comprise a DNA construct which includes a segment of a DNA sequence that encodes a plant quinolate phosphoribosyl transferase mRNA.

A further aspect of the present invention is a method for reducing expression of a quinolate phosphoribosyl transferase gene in a plant cell by growing a plant cell transformed to contain exogenous DNA, where a transcribed strand of the exogenous DNA is complementary to quinolate phosphoribosyl transferase mRNA endogenous to the cell. Transcription of the complementary strand reduces expression of the endogenous quinolate phosphoribosyl gene.

A further aspect of the present invention is a method of producing a tobacco plant having decreased levels of nicotine in leaves of the tobacco plant by growing a tobacco plant with cells that comprise an exogenous DNA sequence, where a transcribed strand of the exogenous DNA sequence is complementary to endogenous quinolate phosphoribosyl transferase messenger RNA in the cells.

A further aspect of the present invention is a method of making a transgenic plant cell having increased quinolate phosphoribosyl transferase (QPRTase) expression, by transforming a plant cell known to express quinolate phosphoribosyl transferase with an exogenous DNA construct which comprises a DNA sequence encoding quinolate phosphoribosyl transferase.

A further aspect of the present invention is a transgenic *Nicotiana* plant having increased quinolate phosphoribosyl transferase (QPRTase) expression, where cells of the transgenic plant comprise an exogenous DNA sequence encoding a plant quinolate phosphoribosyl transferase.

A further aspect of the present invention is a method for increasing expression of a quinolate phosphoribosyl transferase gene in a plant cell, by growing a plant cell transformed to contain exogenous DNA encoding quinolate phosphoribosyl transferase.

A further aspect of the present invention is a method of producing a tobacco plant having increased levels of nicotine in the leaves, by growing a tobacco plant having cells that contain an exogenous DNA sequence that encodes quinolate phosphoribosyl transferase functional in the cells.

BRIEF DESCRIPTION OF THE DRAWINGS

FIG. 2A provides the nucleic acid sequence of NtQPT1 cDNA (SEQ ID NO:1), with the coding sequence (SEQ ID NO:3) shown in capital letters.

FIG. 2B provides the deduced amino acid sequence (SEQ ID NO:2) of the tobacco QPRTase encoded by NtQPT1 cDNA.

FIG. 3 aligns the deduced NtQPT1 amino acid sequence (SEQ ID NO:2) and related sequences of *Rhodospirillum rubrum* (SEQ ID NO:4), *Mycobacterium leprae* (SEQ ID NO:5), *Salmonella typhimurium* (SEQ ID NO:6), *Escherichia coli* (SEQ ID NO:7), human (SEQ ID NO:8), and *Saccharomyces cerevisiae* (SEQ ID NO:9).

DETAILED DESCRIPTION OF THE INVENTION

Figure 1:
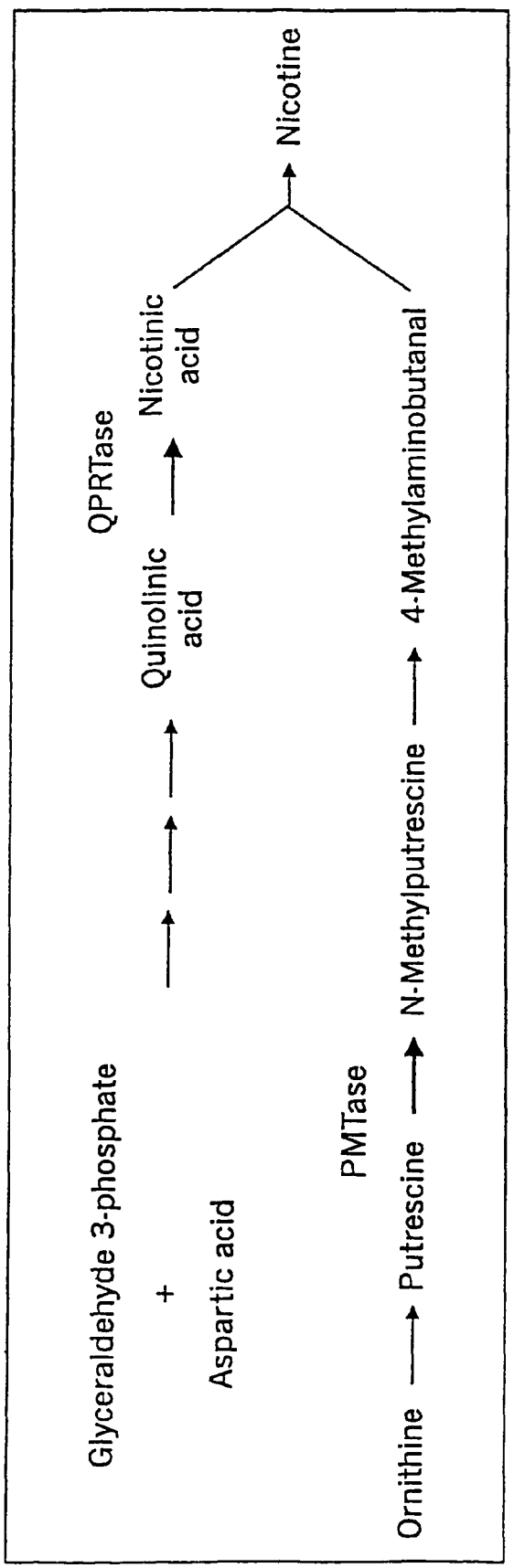
FIG. 1 shows the biosynthetic pathway leading to nicotine. Enzyme activities known to be regulated by Nic1 and Nic2 are QPRTase (quinolate phosphoribosyl transferase) and PMTase (putrescence methyltransferase).

Nicotine is produced in tobacco plants by the condensation of nicotinic acid and 4-methylaminobutanal. The biosynthetic pathway resulting in nicotine production is illustrated in FIG. 1. Two regulatory loci (Nic1 and Nic2) act as co-dominant regulators of nicotine production. Enzyme analyses of roots of single and double Nic mutants show that the activities of two enzymes, quinolate phosphoribosyl transferase (QPRTase) and putrescence methyl transferase (PMTase), are directly proportional to levels of nicotine biosynthesis. A comparison of enzyme activity in tobacco tissues (root and callus) with different capacities for nicotine synthesis shows that QPRTase activity is strictly correlated with nicotine content (Wagner and Wagner, *Planta* 165:532 (1985)). Saunders and Bush (*Plant Physiol* 64:236 (1979) showed that the level of QPRTase in the roots of low nicotine mutants is proportional to the levels of nicotine in the leaves.

The present invention encompasses a novel cDNA sequence (SEQ ID NO:1) encoding a plant quinolate phosphoribosyl transferase (QPRTase) of SEQ ID NO:2. As QPRTase activity is strictly correlated with nicotine content, construction of transgenic tobacco plants in which QPRTase levels are lowered in the plant roots (compared to levels in wild-type plants) result in plants having reduced levels of nicotine in the leaves. The present invention provides methods and nucleic acid constructs for producing such transgenic plants, as well as such transgenic plants. Such methods include the expression of antisense NtQPT1 RNA, which lowers the amount of QPRTase in tobacco roots. Nicotine has additionally been found in non-tobacco species and families of plants, though the amount present is usually much lower than in *N. tabacum*.

The present invention also provides sense and antisense recombinant DNA molecules encoding QPRTase or QPRTase antisense RNA molecules, and vectors comprising those recombinant DNA molecules, as well as transgenic plant cells and plants transformed with those DNA molecules and vectors. Transgenic tobacco cells and plants of this invention are characterized by lower or higher nicotine content than untransformed control tobacco cells and plants.

Tobacco plants with extremely low levels of nicotine production, or no nicotine production, are attractive as recipients for transgenes expressing commercially valuable products such as pharmaceuticals, cosmetic components, or food additives. Tobacco is attractive as a recipient plant for a transgene encoding a desirable product, as tobacco is easily genetically engineered and produces a very large biomass per acre; tobacco plants with reduced resources devoted to nicotine production accordingly will have more resources available for production of transgene products. Methods of transforming tobacco with transgenes producing desired products are known in the art; any suitable technique may be utilized with the low nicotine tobacco plants of the present invention.

Tobacco plants according to the present invention with reduced QPRTase expression and reduced nicotine levels will be desirable in the production of tobacco products having reduced nicotine content. Tobacco plants according to the present invention will be suitable for use in any traditional tobacco product, including but not limited to pipe, cigar and cigarette tobacco, and chewing tobacco, and may be in any form including leaf tobacco, shredded tobacco, or cut tobacco.

The constructs of the present invention may also be useful in providing transgenic plants having increased QPRTase expression and increased nicotine content in the plant. Such constructs, methods using these constructs and the plants so produced may be desirable in the production of tobacco products having altered nicotine content, or in the production of plants having nicotine content increased for its insecticidal effects.

The present inventors have discovered that the TobRD2 gene (see Conkling et al., *Plant Phys.* 93, 1203 (1990)) encodes a *Nicotiana* 20 *tabacum* QPRTase, and provide herein the cDNA sequence of NtQPT1 (formerly termed TobRD2) and the amino acid sequence of the encoded enzyme. Comparisons of the NtQPT1 amino acid sequence with the GenBank database reveal limited sequence similarity to bacterial proteins that encode quinolate phosphoribosyl transferase (QPRTase) (FIG. 3).

Quinolate phosphoribosyl transferase is required for de novo nicotine adenine dinucleotide (NAD) biosynthesis in both prokaryotes and eukaryotes. In tobacco, high levels of QPRTase are detected in roots, but not in leaves. To determine that NtQPT1 encoded QPRTase, the present inventors utilized *Escherichia coli* bacterial strain (TH265), a mutant lacking in quinolate phosphoribosyl transferase (nadC$^-$). This mutant cannot grow on minimal medium lacking nicotinic acid. However, expression of the NtQPT1 protein in this bacterial strain conferred the NadC$^+$ phenotype (FIG. 4), confirming that NtQPT1 encodes QPRTase.

Figure 5:
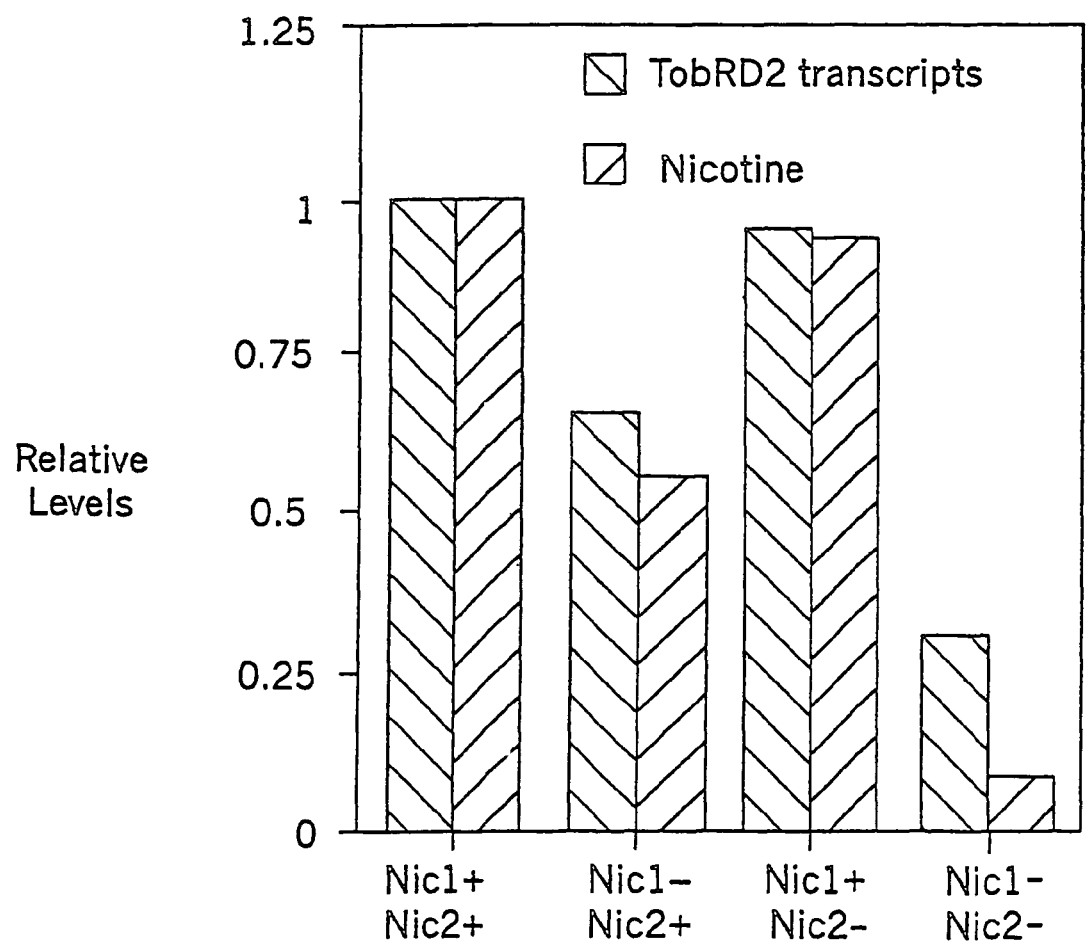
FIG. 5 compares nicotine levels and the relative steady-state NtQTP1 mRNA levels in Nic1 and Nic2 tobacco mutants: wild-type Burley 21 (Nic1/Nic1 Nic2/Nic2); Nic1⁻ Burley 21 (nic1/nic] Nic2/Nic2); Nic2⁻ Burley 21 (Nic1/Nic1 nic2/nic2); and Nic1⁻ Nic2⁻ Burley 21 (nic1/nic1 nic2/nic2). Solid bars indicate mRNA transcript levels; hatched bars indicate nicotine levels.

The present inventors examined the effects of Nic1 and Nic2 mutants in tobacco, and the effects of topping tobacco plants, on NtQPT1 steady-state mRNA levels and nicotine levels. (Removal of apical dominance by topping at onset of flowering is well known to result in increased levels of nicotine biosynthesis and transport in tobacco, and is a standard practice in tobacco production.) If NtQPT1 is in fact involved in nicotine biosynthesis, it would be expected that (1) NtQPT1 mRNA levels would be lower in Nic1/Nic2 double mutants and (2) NtQPT1 mRNA levels would increase after topping. NtQPT1 mRNA levels in Nic1/Nic2 double mutants were found to be approximately 25% that of wild-type (FIG. 5). Further, within six hours of topping, the NTQPT1 mRNA levels in tobacco plants increased about eight-fold. Therefore, NtQPT1 was determined to be a key regulatory gene in the nicotine biosynthetic pathway.

Transgenic Plant Cells and Plants

Regulation of gene expression in plant cell genomes can be achieved by integration of heterologous DNA under the transcriptional control of a promoter which is functional in the host, and in which the transcribed strand of heterologous DNA is complementary to the strand of DNA that is transcribed from the endogenous gene to be regulated. The introduced DNA, referred to as antisense DNA, provides an RNA sequence which is complementary to naturally produced (endogenous) mRNAs and which inhibits expression of the endogenous mRNA. The mechanism of such gene expression regulation by antisense is not completely understood. While not wishing to be held to any single theory, it is noted that one theory of antisense regulation proposes that transcription of antisense DNA produces RNA molecules which bind to and prevent or inhibit transcription of endogenous mRNA molecules.

In the methods of the present invention, the antisense product may be complementary to coding or non-coding (or both) portions of naturally occurring target RNA. The antisense construction may be introduced into the plant cells in any suitable manner, and may be integrated into the plant genome for inducible or constitutive transcription of the antisense sequence. See, e.g., U.S. Pat. Nos. 5,453,566 and 5,107,065 to Shewmaker et al. (incorporated by reference herein in their entirety). As used herein, exogenous or heterologous DNA (or RNA) refers to DNA (or RNA) which has been introduced into a cell (or the cell's ancestor) through the efforts of humans. Such heterologous DNA may be a copy of a sequence which is naturally found in the cell being transformed, or fragments thereof.

To produce a tobacco plant having decreased QPRTase levels, and thus lower nicotine content, than an untransformed control tobacco plant, a tobacco cell may be transformed with an exogenous QPRT antisense transcriptional unit comprising a partial QPRT cDNA sequence, a full-length QPRT cDNA sequence, a partial QPRT chromosomal sequence, or a full-length QPRT chromosomal sequence, in the antisense orientation with appropriate operably linked regulatory sequences. Appropriate regulatory sequences include a transcription initiation sequence ("promoter") operable in the plant being transformed, and a polyadenylation/transcription termination sequence. Standard techniques, such as restriction mapping, Southern blot hybridization, and nucleotide sequence analysis, are then employed to identify clones bearing QPRTase sequences in the antisense orientation, operably linked to the regulatory sequences. Tobacco plants are then regenerated from successfully transformed cells. It is most preferred that the antisense sequence utilized be complementary to the endogenous sequence, however, minor variations in the exogenous and endogenous sequences may be tolerated. It is preferred that the antisense DNA sequence be of sufficient sequence similarity that it is capable of binding to the endogenous sequence in the cell to be regulated, under stringent conditions as described below.

Antisense technology has been employed in several laboratories to create transgenic plants characterized by lower than normal amounts of specific enzymes. For example, plants with lowered levels of chalcone synthase, an enzyme of a flower pigment biosynthetic pathway, have been produced by inserting a chalcone synthase antisense gene into the genome of tobacco and petunia. These transgenic tobacco and petunia plants produce flowers with lighter than normal coloration (Van der Krol et al., "An Anti-Sense Chalcone Synthase Gene in Transgenic Plants Inhibits Flower Pigmentation", *Nature*, 333, pp. 866-69 (1988)). Antisense RNA technology has also been successfully employed to inhibit production of the enzyme polygalacturonase in tomatoes (Smith et al., "Antisense RNA Inhibition of Polygalacturonase Gene Expression in Transgenic Tomatoes", *Nature*, 334, pp. 724-26 (1988); Sheehy et al., "Reduction of Polygalacturonase Activity in Tomato Fruit by Antisense RNA", *Proc. Nat. Acad. Sci. USA*, 85, pp. 8805-09 (1988)), and the small subunit of the enzyme ribulose bisphosphate carboxylase in tobacco (Rodermel et al., "Nuclear-Organelle Interactions: Nuclear Antisense Gene Inhibits Ribulose Bisphosphate Carboxylase Enzyme Levels in Transformed Tobacco Plants", *Cell*, 55, pp. 673-81 (1988)). Alternatively, transgenic plants characterized by greater than normal amounts of a given enzyme may be created by transforming the plants with the gene for that enzyme in the sense (i.e., normal) orientation. Levels of nicotine in the transgenic tobacco plants of the present invention can be detected by standard nicotine assays. Transformed plants in which the level of QPRTase is reduced compared to untransformed control plants will accordingly have a reduced nicotine level compared to the control; transformed plants in which the level of QPRTase is increased compared to untransformed control plants will accordingly have an increased nicotine level compared to the control.

The heterologous sequence utilized in the antisense methods of the present invention may be selected so as to produce an RNA product complementary to the entire QPRTase mRNA sequence, or to a portion thereof. The sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA. Suitable antisense sequences may be from at least about 13 to about 15 nucleotides, at least about 16 to about 21 nucleotides, at least about 20 nucleotides, at least about 30 nucleotides, at least about 50 nucleotides, at least about 75 nucleotides, at least about 100 nucleotides, at least about 125 nucleotides, at least about 150 nucleotides, at least about 200 nucleotides, or more. In addition, the sequences may be extended or shortened on the 3' or 5' ends thereof.

The particular anti-sense sequence and the length of the anti-sense sequence will vary depending upon the degree of inhibition desired, the stability of the anti-sense sequence, and the like. One of skill in the art will be guided in the selection of appropriate QPRTase antisense sequences using techniques available in the art and the information provided herein. With reference to FIG. 2A and SEQ ID NO: 1 herein, an oligonucleotide of the invention may be a continuous fragment of the QPRTase cDNA sequence in antisense orientation, of any length that is sufficient to achieve the desired effects when transformed into a recipient plant cell.

The present invention may also be used in methods of sense co-suppression of nicotine production. Sense DNAs employed in carrying out the present invention are of a length sufficient to, when expressed in a plant cell, suppress the native expression of the plant QPRTase protein as described herein in that plant cell. Such sense DNAs may be essentially an entire genomic or complementary DNA encoding the QPRTase enzyme, or a fragment thereof with such fragments typically being at least 15 nucleotides in length. Methods of ascertaining the length of sense DNA that results in suppression of the expression of a native gene in a cell are available to those skilled in the art.

In an alternate embodiment of the present invention, *Nicotiana* 30 plant cells are transformed with a DNA construct containing a DNA segment encoding an enzymatic RNA molecule (i.e., a "ribozyme"), which enzymatic RNA molecule is directed against (i.e., cleaves) the mRNA transcript of DNA encoding plant QPRTase as described herein. Ribozymes contain substrate binding domains that bind to accessible regions of the target mRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif. Ribozyme cleavage sites within an RNA target may initially be identified by scanning the target molecule for ribozyme cleavage sites (e.g., GUA, GUU or GUC sequences). Once identified, short RNA sequences of 15, 20, 30 or more ribonucleotides corresponding to the region of the target gene containing the cleavage site may be evaluated for predicted structural features. The suitability of candidate targets may also be evaluated by testing their accessibility to hybridization with complimentary oligonucleotides, using ribonuclease protection assays as are known in the art. DNA encoding enzymatic RNA molecules may be produced in accordance with known techniques. See, e.g., T. Cech et al., U.S. Pat. No. 4,987,071; Keene et al., U.S. Pat. No. 5,559,021; Donson et al., U.S. Pat. No. 5,589,367; Torrence et al., U.S. Pat. No. 5,583,032; Joyce, U.S. Pat. No. 5,580,967; Gold et al. U.S. Pat. No. 5,595,877; Wagner et al., U.S. Pat. No. 5,591,601; and U.S. Pat. No. 5,622,854 (the disclosures of which are to be incorporated herein by reference in their entirety). Production of such an enzymatic RNA molecule in a plant cell and disruption of QPRTase protein production reduces QPRTase activity in plant cells in essentially the same manner as production of an antisense RNA molecule: that is, by disrupting translation of mRNA in the cell which produces the enzyme. The term 'ribozyme' is used herein to describe an RNA-containing nucleic acid that functions as an enzyme (such as an endoribonuclease), and may be used interchangeably with 'enzymatic RNA molecule'. The present invention further includes DNA encoding the ribozymes, DNA encoding ribozymes which has been inserted into an expression vector, host cells containing such vectors, and methods of decreasing QPRTase production in plants using ribozymes.

Nucleic acid sequences employed in carrying out the present invention include those with sequence similarity to SEQ ID NO:1, and encoding a protein having quinolate phosphoribosyl transferase activity. This definition is intended to encompass natural allelic variations in QPRTase proteins. Thus, DNA sequences that hybridize to DNA of SEQ ID NO:1 and code for expression of QPRTase, particularly plant QPRTase enzymes, may also be employed in carrying out the present invention.

Multiple forms of tobacco QPRT enzyme may exist. Multiple forms of an enzyme may be due to post-translational modification of a single gene product, or to multiple forms of the NtQPT1 gene.

Conditions which permit other DNA sequences which code for expression of a protein having QPRTase activity to hybridize to DNA of SEQ ID NO:1 or to other DNA sequences encoding the protein given as SEQ ID NO:2 can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA encoding the protein given as SEQ ID NO:2 herein in a standard in situ hybridization assay. See J. Sambrook et al., Molecular Cloning, A Laboratory Manual (2d Ed. 1989)(Cold Spring Harbor Laboratory)). In general, such sequences will be at least 65% similar, 75% similar, 80% similar, 85% similar, 90% similar, or even 95% similar, or more, with the sequence given herein as SEQ ID) NO:1, or DNA sequences encoding proteins of SEQ ID NO:2. (Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.)

Differential hybridization procedures are available which allow for the isolation of cDNA clones whose mRNA levels are as low as about 0.05% of poly(A$^+$)RNA. See M. Conkling et al., *Plant Physiol.* 93, 1203-1211 (1990). In brief, cDNA libraries are screened using single-stranded cDNA probes of reverse transcribed mRNA from plant tissue (e.g., roots and/or leaves). For differential screening, a nitrocellulose or nylon membrane is soaked in 5×SSC, placed in a 96 well suction manifold, 150 µL of stationary overnight culture transferred from a master plate to each well, and vacuum applied until all liquid has passed through the filter. 150 µL of denaturing solution (0.5M NaOH, 1.5 M NaCl) is placed in each well using a multiple pipetter and allowed to sit about 3 minutes. Suction is applied as above and the filter removed and neutralized in 0.5 M Tris-HCl (pH 8.0), 1.5 M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

As used herein, the term 'gene' refers to a DNA sequence that incorporates (1) upstream (5') regulatory signals including the promoter, (2) a coding region specifying the product, protein or RNA of the gene, (3) downstream (3') regions including transcription termination and polyadenylation signals and (4) associated sequences required for efficient and specific expression.

The DNA sequence of the present invention may consist essentially of the sequence provided herein (SEQ ID NO:1), or equivalent nucleotide sequences representing alleles or polymorphic variants of these genes, or coding regions thereof.

Use of the phrase "substantial sequence similarity" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

DNA sequences provided herein can be transformed into a variety of host cells. A variety of suitable host cells, having desirable growth and handling properties, are readily available in the art.

Use of the phrase "isolated" or "substantially pure" in the present specification and claims as a modifier of DNA, RNA, polypeptides or proteins means that the DNA, RNA, polypeptides or proteins so designated have been separated from their in vivo cellular environments through the efforts of human beings. As used herein, a "native DNA sequence" or "natural DNA sequence" means a DNA sequence which can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art. As used herein, a native plant DNA sequence is that which can be isolated from non-transgenic plant cells or tissue. As used herein, a native tobacco DNA sequence is that which can be isolated from non-transgenic tobacco cells or tissue DNA constructs, or "transcription cassettes," of the present invention include, 5, to 3' in the direction of transcription, a promoter as discussed herein, a DNA sequence as discussed herein operatively associated with the promoter, and, optionally, a termination sequence including stop signal for RNA polymerase and a polyadenylation signal for polyadenylase. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator, or native termination signals derived from the same gene as the transcriptional initiation region or derived from a different gene. See, e.g., Rezian et al. (1988) supra, and Rodermel et al. (1988), supra.

The term "operatively associated," as used herein, refers to DNA sequences on a single DNA molecule which are associated so that the function of one is affected by the other. Thus, a promoter is operatively associated with a DNA when it is capable of affecting the transcription of that DNA (i.e., the DNA is under the transcriptional control of the promoter). The promoter is said to be "upstream" from the DNA, which is in turn said to be "downstream" from the promoter.

The transcription cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; may provide complementation, by imparting prototrophy to an auxotrophic host; or may provide a visible phenotype through the production of a novel compound in the plant.

The various fragments comprising the various constructs, transcription cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature as exemplified by J. Sambrook et al., Molecular Cloning, A Laboratory Manual (2d Ed. 1989)(Cold Spring Harbor Laboratory).

Vectors which may be used to transform plant tissue with nucleic acid constructs of the present invention include both *Agrobacterium* vectors and ballistic vectors, as well as vectors suitable for DNA-mediated transformation.

The term 'promoter' refers to a region of a DNA sequence that incorporates the necessary signals for the efficient expression of a coding sequence. This may include sequences to which an RNA polymerase binds but is not limited to such sequences and may include regions to which other regulatory proteins bind together with regions involved in the control of protein translation and may include coding sequences.

Promoters employed in carrying out the present invention may be constitutively active promoters. Numerous constitutively active promoters which are operable in plants are available. A preferred example is the Cauliflower Mosaic Virus (CaMV) 35S promoter which is expressed constitutively in most plant tissues. In the alternative, the promoter may be a root-specific promoter or root cortex specific promoter, as explained in greater detail below.

Antisense sequences have been expressed in transgenic tobacco plants utilizing the Cauliflower Mosaic Virus (CaMV) 35S promoter. See, e.g., Cornelissen et al., "Both RNA Level and Translation Efficiency are Reduced by Anti-Sense RNA in Transgenic Tobacco", *Nucleic Acids Res.* 17, pp. 833-43 (1989); Rezaian et al., "Anti-Sense RNAs of Cucumber Mosaic Virus in Transgenic Plants Assessed for Control of the Virus", *Plant Molecular Biology* 11, pp. 463-71 (1988); Rodermel et al., "Nuclear-Organelle Interactions: Nuclear Antisense Gene Inhibits Ribulose Bisphosphate Carboxylase Enzyme Levels in Transformed Tobacco Plants", *Cell* 55, pp. 673-81 (1988); Smith et al., "Antisense RNA Inhibition of Polygalacturonase Gene Expression in Transgenic Tomatoes", *Nature* 334, pp. 724-26 (1988); Van der Krol et al., "An Anti-Sense Chalcone Synthase Gene in Transgenic Plants Inhibits Flower Pigmentation", *Nature* 333, pp. 866-69 (1988).

Use of the CaMV 35S promoter for expression of QPRTase in the transformed tobacco cells and plants of this invention is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", *Proc. Nat. Acad. Sci. USA* 86, pp. 7890-94 (1989); Pulse et al. "Dissection of 5' Upstream Sequences for Selective Expression of the *Nicotiana plumbaginifolia* rbcS-8B Gene", *Mol. Gen. Genet.* 214, pp. 16-23 (1988)).

Other promoters which are active only in root tissues (root specific promoters) are also particularly suited to the methods of the present invention. See, e.g., U.S. Pat. No. 5,459,252 to Conkling et al.; Yamamoto et al., *The Plant Cell*, 3:371 (1991). The TobRD2 root-cortex specific promoter may also be utilized. See, e.g., U.S. patent application Ser. No. 08/508,786, now allowed, to Conkling et al.; PCT WO 9705261. All patents cited herein are intended to be incorporated herein by reference in their entirety.

The QPRTase recombinant DNA molecules and vectors used to produce the transformed tobacco cells and plants of this invention may further comprise a dominant selectable marker gene. Suitable dominant selectable markers for use in tobacco include, inter alia, antibiotic resistance genes encoding neomycin phosphotransferase (NPTII), hygromycin phosphotransferase (HPT), and chloramphenicol acetyltransferase (CAT). Another well-known dominant selectable marker suitable for use in tobacco is a mutant dihydrofolate reductase gene that encodes methotrexate-resistant dihydrofolate reductase. DNA vectors containing suitable antibiotic resistance genes, and the corresponding antibiotics, are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply.

Methods of making recombinant plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a recombinant plant is regenerated from the transformed plant cell. As explained below, the transforming step is carried out by techniques as are known in the art, including but not limited to bombarding the plant cell with microparticles carrying the transcription cassette, infecting the cell with an *Agrobacterium tumefaciens* containing a Ti plasmid carrying the transcription cassette, or any other technique suitable for the production of a transgenic plant.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et al. discloses a binary *Agrobacterium* vector (i.e., one in which the *Agrobacterium* contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 μm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art. Fusion of tobacco protoplasts with DNA-containing liposomes or via electroporation is known in the art. (Shillito et al., "Direct Gene Transfer to Protoplasts of Dicotyledonous and Monocotyledonous Plants by a Number of Methods, Including Electroporation", *Methods in Enzymology* 153, pp. 3 13-36 (1987)).

As used herein, transformation refers to the introduction of exogenous DNA into cells, so as to produce transgenic cells stably transformed with the exogenous DNA.

Transformed cells are induced to regenerate intact tobacco plants through application of tobacco cell and tissue culture techniques that are well known in the art. The method of plant regeneration is chosen so as to be compatible with the method of transformation. The stable presence and the orientation of the QPRTase sequence in transgenic tobacco plants can be verified by Mendelian inheritance of the QPRTase sequence, as revealed by standard methods of DNA analysis applied to progeny resulting from controlled crosses. After regeneration of transgenic tobacco plants from transformed cells, the introduced DNA sequence is readily transferred to other tobacco varieties through conventional plant breeding practices and without undue experimentation.

For example, to analyze the segregation of the transgene, regenerated transformed plants ($R_0$) may be grown to maturity, tested for nicotine levels, and selfed to produce $R_1$ plants. A percentage of $R_1$ plants carrying the transgene are homozygous for the transgene. To identify homozygous $R_1$ plants, transgenic $R_1$ plants are grown to maturity and selfed. Homozygous $RI_1$, plants will produce $R_2$ progeny where each progeny plant carries the transgene; progeny of heterozygous $RI_1$, plants will segregate 3:1.

As nicotine serves as a natural pesticide which helps protect tobacco plants from damage by pests. It may therefore be desirable to additionally transform low or no nicotine plants produced by the present methods with a transgene (such as *Bacillus thuringiensis*) that will confer additional insect protection.

A preferred plant for use in the present methods are species of *Nicotiana*, or tobacco, including *N tabacum, N rustica* and *N glutinosa*. Any strain or variety of tobacco may be used. Preferred are strains that are already low in nicotine content, such as Nic1/Nic2 double mutants.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as nptII) can be associated with the transcription cassette to assist in breeding.

In view of the foregoing, it will be apparent that plants which may be employed in practicing the present invention include those of the genus *Nicotiana*.

Those familiar with the recombinant DNA methods described above will recognize that one can employ a full-length QPRTase cDNA molecule or a full-length QPRTase chromosomal gene, joined in the sense orientation, with appropriate operably linked regulatory sequences, to construct transgenic tobacco cells and plants. (Those of skill in the art will also recognize that appropriate regulatory sequences for expression of genes in the sense orientation include any one of the known eukaryotic translation start sequences, in addition to the promoter and polyadenylation/transcription termination sequences described above). Such transformed tobacco plants are characterized by increased levels of QPRTase, and thus by higher nicotine content than untransformed control tobacco plants.

It should be understood, therefore, that use of QPRTase DNA sequences to decrease or to increase levels of QPRT enzyme, and thereby to decrease or increase the nicotine content in tobacco plants, falls within the scope of the present invention.

As used herein, a crop comprises a plurality of plants of the present invention, and of the same genus, planted together in an agricultural field. By "agricultural field" is meant a common plot of soil or a greenhouse. Thus, the present invention provides a method of producing a crop of plants having altered QPTRase activity and thus having increased or decreased nicotine levels, compared to a similar crop of non-transformed plants of the same species and variety.

The examples which follow are set forth to illustrate the present invention, and are not to be construed as limiting thereof.

EXAMPLE 1

Isolation and Sequencing

TobRD2 cDNA (Conkling et al., *Plant Phys.* 93, 1203 (1990)) was sequenced and is provided herein as SEQ ID NO: 1, and the deduced amino acid sequence as SEQ ID No:2. The deduced amino acid sequence was predicted to be a cytosolic protein. Although plant QPTase genes have not been reported, comparisons of the NtPT1 amino acid sequence with the GenBank database (FIG. 3) revealed limited sequence similarity to certain bacterial and other proteins; quinolate phosphoribosyl transferase (QPRTase) activity has been demonstrated for the *S. typhimurium, E. coli.* and *N tabacum* genes. The NTQPT1 encoded QPTase has similarity to the deduced peptide fragment encoded by an *Arabidopsis* EST (expression sequence tag) sequence (Genbank Accession number F20096), which may represent part of an *Arabidopsis* QPTase gene.

EXAMPLE 2

In-Situ Hybridizations

To determine the spatial distribution of TobRD2 mRNA transcripts in the various tissues of the root, in situ hybridizations were performed in untransformed plants. In-situ hybridizations of antisense strand of TobRD2 to the TobRiD2 mRNA in root tissue was done using techniques as described in Meyerowitz, *Plant Mol. Bid. Rep.* 5,242 (1987) and Smith et al., *Plant Mol. Biol. Rep.* 5, 237 (1987). Seven day old tobacco (*Nicotiana tabacum*) seedling roots were fixed in phosphate-buffered glutaraldehyde, embedded in Paraplast Plus (Monoject Inc., St. Louis, Mo.) and sectioned at 8 mm thickness to obtain transverse as well as longitudinal sections. Antisense TobRD2 transcripts, synthesized in vitro in the presence of 355-ATP, were used as probes. The labeled RNA was hydrolyzed by alkaline treatment to yield 100 to 200 base mass average length prior to use.

Hybridizations were done in 50% formamide for 16 hours at 42° C., with approximately $5 \times 10^6$ counts-per-minute (cpm) labeled RNA per milliliter of hybridization solution. After exposure, the slides were developed and visualized under bright and dark field microscopy. The hybridization signal was localized to the cortical layer of cells in the roots (results not shown). Comparison of both bright and dark field images of the same sections localized TobRD2 transcripts to the parenchymatous cells of the root cortex. No hybridization signal was visible in the epidermis or the stele.

EXAMPLE 3

TobRD2 mRNA Levels in Nic1 and Nic2 Tobacco Mutants and Correlation to Nicotine Levels TobRD2 steady-state mRNA levels were examined in Nic1 and Nic2 mutant tobacco plants. Nic1 and Nic2 are known to regulate quinolate phosphoribosyl transferase activity and putrescence methyl-transferase activity, and are co-dominant regulators of nicotine production. The present results are illustrated in FIGS. 5A and 5B show that TobRD2 expression is regulated by Nic1 and Nic2.

RNA was isolated from the roots of wild-type Burley 21 tobacco plants (Nic1/Nic1 Nic2/Nic2); roots of Nic1– Burley 21 (nic1/nic1 Nic2/Nic2); roots of Nic2– Burley 21 (Nic1/Nic] nic2/nic2); and roots of Nic1Nic2– Burley 21 (nic1/nic1 nic2/nic2).

Four Burley 21 tobacco lines (nic) were grown from seed in soil for a month and transferred to hydroponic chambers in aerated nutrient solution in a greenhouse for one month. These lines were isogenic, except for the two low-nicotine loci, and had genotypes of Nic1/Nic1 Nic2/Nic2, Nic1/Nic1 nic2/nic2, nic1/nic1 Nic2/Nic2, nic1/nic1 nic2/nic2. Roots were harvested from about 20 plants for each genotype and pooled for RNA isolation. Total RNA (1 [μg) from each genotype was electrophoresed through a 1% agarose gel containing 1.1 M formaldehyde and transferred to a nylon membrane according to Sambrook et al. (1989). The membranes were hybridized with $^{32}$P-labeled TobRD2 cDNA fragments. Relative intensity of TobRD2 transcripts were measured by densitometry. FIG. 5 (solid bars) illustrates the relative transcript levels (compared to Nic1/Nic1 Nic2/Nic2) for each of the four genotypes. The relative nicotine content (compared to Nic1/Nic1 Nic2/Nic2) of the four genotypes is shown by the hatched bars.

FIG. 5 graphically compares the relative steady state TobRD2 5 mRNA level, using the level found in wild-type Burley 21 (Nic1/Nic1 Nic2/Nic2) as the reference amount. TobRD2 mRNA levels in Nic1/Nic2 double mutants were approximately 25% that of wild-type tobacco. FIG. 5B further compares the relative levels of nicotine in the near isogenic lines of tobacco studied in this example (solid bars indicate TobRD2 transcript levels; hatched bars indicate nicotine level). There was a close correlation between nicotine levels and TobRD2 transcript levels.

EXAMPLE 4

The Effect of Topping on TobRD2 mRNA Levels

It is well known in the art that removal of the flower head of a tobacco plant (topping) increases root growth and increases nicotine content of the leaves of that plant. Topping of the plant and is a standard practice in commercial tobacco cultivation, and the optimal time for topping a given tobacco plant under a known set of growing conditions can readily be determined by one of ordinary skill in the art.

Figure 6:
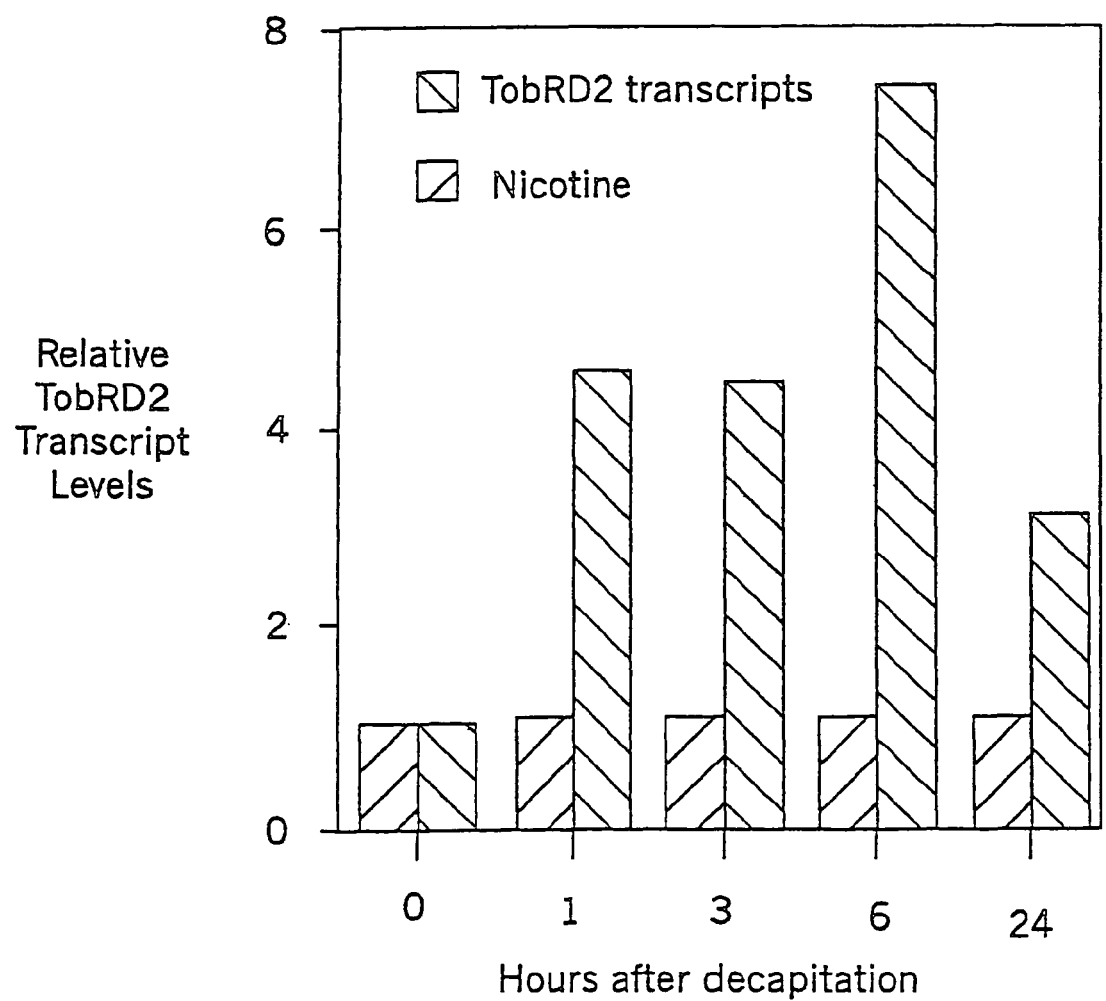
FIG. 6 charts the relative levels of NtQPT1 mRNA over time in topped tobacco plants compared to non-topped control plants. Solid bars indicate mRNA transcript levels; hatched bars indicate nicotine levels.

Tobacco plants (*N tabacum* SRI) were grown from seed in soil for a month and transferred to pots containing sand. Plants were grown in a greenhouse for another two months until they started setting flowers. Flower heads and two nodes were then removed from four plants (topping). A portion of the roots was harvested from each plant after the indicated time and pooled for RNA extraction. Control plants were not decapitated. Total RNA (1 μg) from each time point was electrophoresed through a 1% agarose gel containing 1.1M formaldehyde and transferred to a nylon membrane according to Sambrook, et al. (1989). The membranes were hybridized with $^{32}$P-labeled TobRD2 cDNA fragments. Relative intensity of TobRD2 transcripts were measured by densitometry. FIG. 6 illustrates the relative transcript levels (compared to zero time) for each time-point with topping (solid bars) or without topping (hatched bars).

Relative TobRD2 levels were determined in root tissue over 24 hours; results are shown in FIG. 6 (solid bars indicate TobRD2 transcript levels in topped plants; hatched bars indicate the TobRD2 transcript levels in non-topped controls). Within six hours of topping of tobacco plants, mRNA levels of TobRD2 increased approximately eight-fold in the topped plants; no increase was seen in control plants over the same time period.

EXAMPLE 5

Complementation of Bacterial Mutant Lacking QPRTase with DNA of SEQ ID NO:1

*Escherichia coli* strain TH265 is a mutant lacking quinolate phosphoribosyl transferase (nadC−), and therefore cannot grow on media lacking nicotinic acids.

TH265 cells were transformed with an expression vector (pWS161) containing DNA of SEQ ID NO):1, or transformed with the expression vector (pKK233) only. Growth of the transformed bacteria was compared to growth of TH265 (pKK233) transformants, and to growth of the untransformed TH265 nadC− mutant. Growth was compared on ME minimal media (lacking nicotinic acid) and on ME minimal media with added nicotinic acid.

The *E. coli* strain with the QPTase mutation (nadC), TH265, was kindly provided by Dr. K. T. Hughes (Hughes et al., *J. Bact.* 175:479 (1993). The cells were maintained on LB media and competent cells prepared as described in Sambrook et al (1989). An expression plasmid was constructed in pKK2233 (Brosius, 1984) with the TobRD2 cDNA cloned under the control of the Tac promoter. The resulting plasmid, pWS161, was transformed into TH265 cells. The transformed cells were then plated on minimal media (Vogel and Bonner, 1956) agar plates with or without nicotinic acid (0.0002%) as supplement. TH265 cells alone and TH265 transformed with pKK2233 were plated on similar plates for use as controls.

Figure 4:
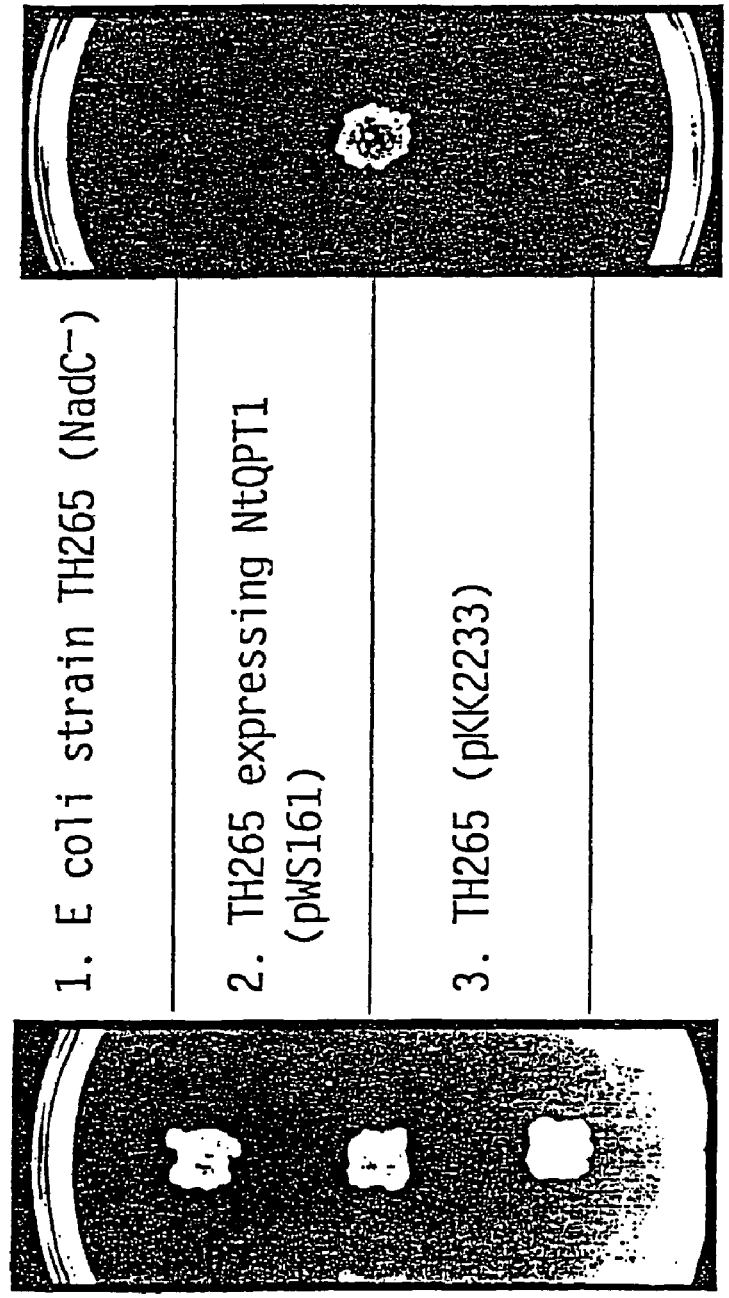
FIG. 4 shows the results of complementation of an *Escherichia coli* mutant lacking quinolate phosphoribosyl transferase (TH265) with NTQPT1 cDNA. Cells were transformed with an expression vector carrying NtQPT1; growth of transformed TH265 cells expressing NtQPT1 on minimal medium lacking nicotinic acid demonstrated that NtQPT1 encodes QPRTase.

Results are shown in FIG. 4. Only the TH265 transformed with DNA of SEQ ID NO:1 grew in media lacking nicotinic acid. These results show that expression of DNA of SEQ ID NO:1 in TH265 bacterial cells conferred the NadC+ phenotype on these cells, confirming that this sequence encodes QPRTase. The TobRID2 nomenclature was thus changed to NtQPT1.

EXAMPLE 6

Transformation of Tobacco Plants

DNA of SEQ ID NO: 1, in antisense orientation, is operably linked to a plant promoter (CaMV 35S or TobRD2 root-cortex specific promoter) to produce two different DNA cassettes: CaMV35S promoter/antisense SEQ ID NO: 1 and TobRD2 promoter/antisense SEQ ID NO: 1.

A wild-type tobacco line and a low-nicotine tobacco line are selected for transformation, e.g., wild-type Burley 21 tobacco (Nic1+/Nic2+) and homozygous nic1− /nic2− Burley 21. A plurality of tobacco plant cells from each line are transformed using each of the DNA cassettes. Transformation is conducted using an *Agrobacterium* vector, e.g., an *Agrobacterium*-binary vector carrying Ti-border sequences and the nptII gene (conferring resistance to kanamycin and under the control of the nos promoter (nptII)).

Transformed cells are selected and regenerated into transgenic tobacco plants ($R_0$). The $R_0$ plants are grown to maturity and tested for levels of nicotine; a subset of the transformed tobacco plants exhibit significantly lower levels of nicotine compared to non-transformed control plants.

$R_0$ plants are then selfed and the segregation of the transgene is analyzed in $R_1$ progeny. $RI_1$ progeny are grown to maturity and selfed; segregation of the transgene among $RI_2$ progeny indicate which $RI_1$ plants are homozygous for the transgene.

That which is claimed:

1. A tobacco product comprising a transgenic plant cell from a transgenic tobacco plant of the genus *Nicotiana* having reduced quinolate phosphoribosyl transferase (QPRTase) production relative to a non-transformed control plant, said transgenic plant comprising transgenic plant cells comprising a heterologous nucleic acid;
   comprising a nucleotide sequence selected from the group consisting of:
   (a) the nucleotide sequence of SEQ ID NO:1;
   (b) a nucleotide sequence that encodes a quinolate phosphoribosyl transferase enzyme having the amino acid sequence of SEQ ID NO:2;
   (c) a nucleotide sequence that is at least 95% identical to the nucleotide sequence of (a) or (b) above and that encodes a quinolate phosphoribosyl transferase enzyme; and
   (d) a nucleotide sequence that differs from the nucleotide sequence of (a) or (b) above due to the degeneracy of the genetic code and that encodes a quinolate phosphoribosyl transferase enzyme.

2. A tobacco product comprising a transgenic plant cell from a transgenic tobacco plant of the genus *Nicotiana* having a decreased level of nicotine in leaves of said plant relative to a non-transformed control plant, wherein said plant comprises transgenic plant cells comprising a heterologous nucleic acid,
   comprising a nucleotide sequence selected from the group consisting of:
   (a) the nucleotide sequence of SEQ ID NO:1;
   (b) a nucleotide sequence that encodes a quinolate phosphoribosyl transferase enzyme having the amino acid sequence of SEQ ID NO:2;
   (c) a nucleotide sequence that is at least 95% identical to the nucleotide sequence of (a) or (b) above and that encodes a quinolate phosphoribosyl transferase enzyme; and
   (d) a nucleotide sequence that differs from the nucleotide sequence of (a) or (b) above due to the degeneracy of the genetic code and that encodes a quinolate phosphoribosyl transferase enzyme.

3. The tobacco product of claim 1, wherein said heterologous nucleic acid is in antisense orientation.

4. The tobacco product of claim 2, wherein said heterologous nucleic acid is in antisense orientation.

5. The tobacco product of claim 1, wherein said heterologous nucleic acid is in sense orientation.

6. The tobacco product of claim 2, wherein said heterologous nucleic acid is in sense orientation.

7. A tobacco product comprising a transgenic plant cell from a transgenic plant of the genus *Nicotiana* having reduced quinolate phosphoribosyl transferase (QPRTase) production relative to a non-transformed control plant, wherein said transgenic plant is a progeny of the plant of claim 1.

8. A tobacco product comprising a transgenic plant cell from a transgenic plant of the genus *Nicotiana* having reduced nicotine in leaves of said plant, wherein said transgenic plant is a progeny of the plant of claim 2.

9. The tobacco product of claim 1, wherein the tobacco product is selected from the group consisting of a cigarette, cigarette tobacco, cigar tobacco, a cigar, pipe tobacco, chewing tobacco, leaf tobacco, shredded tobacco and cut tobacco.

10. The tobacco product of claim 2, wherein the tobacco product is selected from the group consisting of a cigarette, cigarette tobacco, cigar tobacco, a cigar, pipe tobacco, chewing tobacco, leaf tobacco, shredded tobacco and cut tobacco.

11. The tobacco product of claim 3, wherein the tobacco product is selected from the group consisting of a cigarette, cigarette tobacco, cigar tobacco, a cigar, pipe tobacco, chewing tobacco, leaf tobacco, shredded tobacco and cut tobacco.

12. The tobacco product of claim 4, wherein the tobacco product is selected from the group consisting of a cigarette, cigarette tobacco, cigar tobacco, a cigar, pipe tobacco, chewing tobacco, leaf tobacco, shredded tobacco and cut tobacco.

13. The tobacco product of claim 5, wherein the tobacco product is selected from the group consisting of a cigarette, cigarette tobacco, cigar tobacco, a cigar, pipe tobacco, chewing tobacco, leaf tobacco, shredded tobacco and cut tobacco.

14. The tobacco product of claim 6, wherein the tobacco product is selected from the group consisting of a cigarette, cigarette tobacco, cigar tobacco, a cigar, pipe tobacco, chewing tobacco, leaf tobacco, shredded tobacco and cut tobacco.

15. The tobacco product of claim 7, wherein the tobacco product is selected from the group consisting of a cigarette, cigarette tobacco, cigar tobacco, a cigar, pipe tobacco, chewing tobacco, leaf tobacco, shredded tobacco and cut tobacco.

16. The tobacco product of claim 8, wherein the tobacco product is selected from the group consisting of a cigarette, cigarette tobacco, cigar tobacco, a cigar, pipe tobacco, chewing tobacco, leaf tobacco, shredded tobacco and cut tobacco.

* * * * *

UNITED STATES PATENT AND TRADEMARK OFFICE
CERTIFICATE OF CORRECTION

| | |
|---|---|
| PATENT NO. | : 7,795,509 B2 |
| APPLICATION NO. | : 11/416887 |
| DATED | : September 14, 2010 |
| INVENTOR(S) | : Conkling et al. |

It is certified that error appears in the above-identified patent and that said Letters Patent is hereby corrected as shown below:

On Title Page:
Item (56) References Cited, Other Publications, line 47 "Brunnemann et al.":
 Please correct "(977)" to read -- (1977) --

Other Publications, Page 5, left column, line 1 "Hamill, et al.":
 Please correct "ornthine" to read -- ornithine --

Other Publications, Page 5, right column, line 58 "Akimoto et al.":
 Please correct "Transctiption" to read -- Transcription --

Other Publications, Page 10, left column, line 14 "Hecht et al.":
 Please correct "298302" to read -- 298-302 --

Other Publications, Page 11, left column, line 65 "Shoji et al.":
 Please correct "931" to read -- 831--

Signed and Sealed this
Twenty-sixth Day of April, 2011

David J. Kappos
*Director of the United States Patent and Trademark Office*

SEQUENCE LISTING

<160> NUMBER OF SEQ ID NOS: 9

<210> SEQ ID NO 1
<211> LENGTH: 1399
<212> TYPE: DNA
<213> ORGANISM: Nicotiana tabacum
<220> FEATURE:
<221> NAME/KEY: CDS
<222> LOCATION: (52)..(1104)

<400> SEQUENCE: 1

```
caaaaactat tttccacaaa attcatttca caaccccccc aaaaaaaaac c atg ttt        57
                                                         Met Phe
                                                           1 aga gct att cct ttc act gct aca gtg cat cct tat gca att aca gct       105
Arg Ala Ile Pro Phe Thr Ala Thr Val His Pro Tyr Ala Ile Thr Ala
        5                  10                  15 cca agg ttg gtg gtg aaa atg tca gca ata gcc acc aag aat aca aga       153
Pro Arg Leu Val Val Lys Met Ser Ala Ile Ala Thr Lys Asn Thr Arg
 20                  25                  30 gtg gag tca tta gag gtg aaa cca cca gca cac cca act tat gat tta       201
Val Glu Ser Leu Glu Val Lys Pro Pro Ala His Pro Thr Tyr Asp Leu
 35                  40                  45                  50 aag gaa gtt atg aaa ctt gca ctc tct gaa gat gct ggg aat tta gga       249
Lys Glu Val Met Lys Leu Ala Leu Ser Glu Asp Ala Gly Asn Leu Gly
                 55                  60                  65 gat gtg act tgt aag gcg aca att cct ctt gat atg gaa tcc gat gct       297
Asp Val Thr Cys Lys Ala Thr Ile Pro Leu Asp Met Glu Ser Asp Ala
             70                  75                  80 cat ttt cta gca aag gaa gac ggg atc ata gca gga att gca ctt gct       345
His Phe Leu Ala Lys Glu Asp Gly Ile Ile Ala Gly Ile Ala Leu Ala
         85                  90                  95 gag atg ata ttc gcg gaa gtt gat cct tca tta aag gtg gag tgg tat       393
Glu Met Ile Phe Ala Glu Val Asp Pro Ser Leu Lys Val Glu Trp Tyr
    100                 105                 110 gta aat gat ggc gat aaa gtt cat aaa ggc ttg aaa ttt ggc aaa gta       441
Val Asn Asp Gly Asp Lys Val His Lys Gly Leu Lys Phe Gly Lys Val
115                 120                 125                 130 caa gga aac gct tac aac att gtt ata gct gag agg gtt gtt ctc aat       489
Gln Gly Asn Ala Tyr Asn Ile Val Ile Ala Glu Arg Val Val Leu Asn
                135                 140                 145 ttt atg caa aga atg agt gga ata gct aca cta act aag gaa atg gca       537
Phe Met Gln Arg Met Ser Gly Ile Ala Thr Leu Thr Lys Glu Met Ala
            150                 155                 160 gat gct gca cac cct gct tac atc ttg gag act agg aaa act gct cct       585
Asp Ala Ala His Pro Ala Tyr Ile Leu Glu Thr Arg Lys Thr Ala Pro
        165                 170                 175 gga tta cgt ttg gtg gat aaa tgg gcg gta ttg atc ggt ggg ggg aag       633
Gly Leu Arg Leu Val Asp Lys Trp Ala Val Leu Ile Gly Gly Gly Lys
    180                 185                 190 aat cac aga atg ggc tta ttt gat atg gta atg ata aaa gac aat cac       681
Asn His Arg Met Gly Leu Phe Asp Met Val Met Ile Lys Asp Asn His
195                 200                 205                 210 ata tct gct gct gga ggt gtc ggc aaa gct cta aaa tct gtg gat cag       729
Ile Ser Ala Ala Gly Gly Val Gly Lys Ala Leu Lys Ser Val Asp Gln
                215                 220                 225 tat ttg gag caa aat aaa ctt caa ata ggg gtt gag gtt gaa acc agg       777
Tyr Leu Glu Gln Asn Lys Leu Gln Ile Gly Val Glu Val Glu Thr Arg
            230                 235                 240
```

```
aca att gaa gaa gta cgt gag gtt cta gac tat gca tct caa aca aag    825
Thr Ile Glu Glu Val Arg Glu Val Leu Asp Tyr Ala Ser Gln Thr Lys
        245                 250                 255 act tcg ttg act agg ata atg ctg gac aat atg gtt gtt cca tta tct    873
Thr Ser Leu Thr Arg Ile Met Leu Asp Asn Met Val Val Pro Leu Ser
260                 265                 270 aac gga gat att gat gta tcc atg ctt aag gag gct gta gaa ttg atc    921
Asn Gly Asp Ile Asp Val Ser Met Leu Lys Glu Ala Val Glu Leu Ile
275                 280                 285                 290 aat ggg agg ttt gat acg gag gct tca gga aat gtt acc ctt gaa aca    969
Asn Gly Arg Phe Asp Thr Glu Ala Ser Gly Asn Val Thr Leu Glu Thr
                295                 300                 305 gta cac aag att gga caa act ggt gtt acc tac att tct agt ggt gcc   1017
Val His Lys Ile Gly Gln Thr Gly Val Thr Tyr Ile Ser Ser Gly Ala
        310                 315                 320 ctg acg cat tcc gtg aaa gca ctt gac att tcc ctg aag atc gat aca   1065
Leu Thr His Ser Val Lys Ala Leu Asp Ile Ser Leu Lys Ile Asp Thr
        325                 330                 335 gag ctc gcc ctt gaa gtt gga agg cgt aca aaa cga gca tgagcgccat    1114
Glu Leu Ala Leu Glu Val Gly Arg Arg Thr Lys Arg Ala
340                 345                 350 tacttctgct atagggttgg agtaaaagca gctgaatagc tgaaggtgc  aaataagaat  1174 cattttacta gttgtcaaac aaaagatcct tcactgtgta atcaaacaaa aagatgtaaa  1234
ttgctggaat atctcagatg ctctttttcc aaccttattg cttgagttgg taatttcatt  1294
atagctttgt tttcatgttt catggaattt gttacaatga aaatacttga tttataagtt  1354
tggtgtatgt aaaattctgt gttacttcaa atattttgag atgtt               1399

<210> SEQ ID NO 2
<211> LENGTH: 351
<212> TYPE: PRT
<213> ORGANISM: Nicotiana tabacum

<400> SEQUENCE: 2

Met Phe Arg Ala Ile Pro Phe Thr Ala Thr Val His Pro Tyr Ala Ile
1               5                   10                  15

Thr Ala Pro Arg Leu Val Val Lys Met Ser Ala Ile Ala Thr Lys Asn
                20                  25                  30

Thr Arg Val Glu Ser Leu Glu Val Lys Pro Pro Ala His Pro Thr Tyr
            35                  40                  45

Asp Leu Lys Glu Val Met Lys Leu Ala Leu Ser Glu Asp Ala Gly Asn
        50                  55                  60

Leu Gly Asp Val Thr Cys Lys Ala Thr Ile Pro Leu Asp Met Glu Ser
65                  70                  75                  80

Asp Ala His Phe Leu Ala Lys Glu Asp Gly Ile Ile Ala Gly Ile Ala
                85                  90                  95

Leu Ala Glu Met Ile Phe Ala Glu Val Asp Pro Ser Leu Lys Val Glu
            100                 105                 110

Trp Tyr Val Asn Asp Gly Asp Lys Val His Lys Gly Leu Lys Phe Gly
        115                 120                 125

Lys Val Gln Gly Asn Ala Tyr Asn Ile Val Ile Ala Glu Arg Val Val
    130                 135                 140

Leu Asn Phe Met Gln Arg Met Ser Gly Ile Ala Thr Leu Thr Lys Glu
145                 150                 155                 160

Met Ala Asp Ala Ala His Pro Ala Tyr Ile Leu Glu Thr Arg Lys Thr
                165                 170                 175
```

```
Ala Pro Gly Leu Arg Leu Val Asp Lys Trp Ala Val Leu Ile Gly Gly
            180                 185                 190
Gly Lys Asn His Arg Met Gly Leu Phe Asp Met Val Met Ile Lys Asp
        195                 200                 205
Asn His Ile Ser Ala Ala Gly Val Gly Lys Ala Leu Lys Ser Val
        210                 215                 220
Asp Gln Tyr Leu Glu Gln Asn Lys Leu Gln Ile Gly Val Glu Val Glu
225                 230                 235                 240
Thr Arg Thr Ile Glu Glu Val Arg Glu Val Leu Asp Tyr Ala Ser Gln
            245                 250                 255
Thr Lys Thr Ser Leu Thr Arg Ile Met Leu Asp Asn Met Val Val Pro
        260                 265                 270
Leu Ser Asn Gly Asp Ile Asp Val Ser Met Leu Lys Glu Ala Val Glu
        275                 280                 285
Leu Ile Asn Gly Arg Phe Asp Thr Glu Ala Ser Gly Asn Val Thr Leu
        290                 295                 300
Glu Thr Val His Lys Ile Gly Gln Thr Gly Val Thr Tyr Ile Ser Ser
305                 310                 315                 320
Gly Ala Leu Thr His Ser Val Lys Ala Leu Asp Ile Ser Leu Lys Ile
            325                 330                 335
Asp Thr Glu Leu Ala Leu Glu Val Gly Arg Arg Thr Lys Arg Ala
        340                 345                 350

<210> SEQ ID NO 3
<211> LENGTH: 1053
<212> TYPE: DNA
<213> ORGANISM: Nicotiana tabacum

<400> SEQUENCE: 3
atgtttagag ctattccttt cactgctaca gtgcatcctt atgcaattac agctccaagg      60
ttggtggtga aaatgtcagc aatagccacc aagaatacaa gagtggagtc attagaggtg     120
aaaccaccag cacacccaac ttatgattta aaggaagtta tgaaacttgc actctctgaa     180
gatgctggga atttaggaga tgtgacttgt aaggcgacaa ttcctcttga tatggaatcc     240
gatgctcatt ttctagcaaa ggaagacggg atcatagcag aattgcact tgctgagatg     300
atattcgcgg aagttgatcc ttcattaaag gtggagtggt atgtaaatga tggcgataaa     360
gttcataaag gcttgaaatt tggcaaagta caaggaaacg cttacaacat tgttatagct     420
gagagggttg ttctcaattt tatgcaaaga atgagtggaa tagctacact aactaaggaa     480
atggcagatg ctgcacaccc tgcttacatg ttggagacta ggaaaactgc tcctggatta     540
cgtttggtgg ataaatgggc ggtattgatc ggtgggggga agaatcacag aatgggctta     600
tttgatatgg taatgataaa agacaatcac atatctgctg ctggaggtgt cggcaaagct     660
ctaaaatctg tggatcagta tttggagcaa aataaacttc aaataggggt tgaggttgaa     720
accaggacaa ttgaagaagt acgtgaggtt ctagactatg catctcaaac aaagacttcg     780
ttgactagga taatgctgga caatatggtt gttccattat ctaacggaga tattgatgta     840
tccatgctta aggaggctgt agaattgatc aatgggaggt ttgatacgga ggcttcagga     900
aatgttaccc ttgaaacagt acacaagatt ggacaaactg gtgttaccta catttctagt     960
ggtgccctga cgcattccgt gaaagcactt gacatttccc tgaagatcga tacagagctc    1020
gcccttgaag ttggaaggcg tacaaaacga gca                                 1053

<210> SEQ ID NO 4
```

<211> LENGTH: 296
<212> TYPE: PRT
<213> ORGANISM: Rhodospirillum rubrum

<400> SEQUENCE: 4

Met Arg Pro Asn His Pro Val Ala Ala Leu Ser Pro Phe Ala Ile Asp
1               5                   10                  15

Glu Ala Val Arg Arg Ala Leu Ala Glu Asp Leu Gly Arg Ala Gly Asp
            20                  25                  30

Ile Thr Ser Thr Ala Thr Ile Pro Ala Ala Thr Arg Ala His Ala Arg
        35                  40                  45

Phe Val Ala Arg Gln Pro Gly Ile Leu Ala Gly Leu Gly Cys Ala Arg
    50                  55                  60

Ser Ala Phe Ala Leu Leu Asp Asp Thr Val Thr Phe Thr Thr Pro Leu
65                  70                  75                  80

Glu Asp Gly Ala Glu Ile Ala Ala Gly Gln Thr Val Ala Glu Val Ala
                85                  90                  95

Gly Ala Ala Arg Thr Ile Leu Ala Ala Glu Arg Thr Ala Leu Asn Phe
            100                 105                 110

Leu Gly His Leu Ser Gly Ile Ala Thr Arg Thr Arg Phe Gly Asp
        115                 120                 125

Ala Ile Ala His Thr Arg Ala Arg Leu Thr Cys Thr Arg Lys Thr Thr
    130                 135                 140

Pro Gly Leu Arg Gly Leu Glu Lys Tyr Ala Val Arg Cys Gly Gly Gly
145                 150                 155                 160

Ser Asn His Arg Phe Gly Leu Asp Asp Ala Val Leu Ile Lys Asp Asn
                165                 170                 175

His Ile Ala Val Ala Gly Gly Val Ser Ala Ala Leu Ser Arg Ala Arg
            180                 185                 190

Ala Gly Val Gly His Met Val Arg Ile Glu Ile Glu Val Asp Thr Leu
        195                 200                 205

Glu Gln Leu Ala Glu Val Leu Ala Val Gly Gly Ala Glu Val Val Leu
    210                 215                 220

Leu Asp Asn Met Asp Ala Pro Thr Leu Thr Arg Ala Val Asp Met Val
225                 230                 235                 240

Ala Gly Arg Leu Val Thr Glu Ala Ser Gly Gly Val Ser Leu Asp Thr
                245                 250                 255

Ile Ala Ala Leu Ala Glu Ser Gly Val Asp Tyr Ile Ser Val Gly Ala
            260                 265                 270

Leu Thr His Ser Val Thr Thr Leu Asp Ile Gly Leu Asp Ile Val Val
        275                 280                 285

Ala Pro Pro Lys Ala Glu Arg Ala
    290                 295

<210> SEQ ID NO 5
<211> LENGTH: 286
<212> TYPE: PRT
<213> ORGANISM: Mycobacterium leprae

<400> SEQUENCE: 5

Met Ile Met Leu Ser Asp Cys Glu Phe Asp Ala Ala Arg Asp Thr Ile
1               5                   10                  15

Arg Arg Ala Leu His Glu Asp Leu Arg Tyr Gly Leu Asp Ile Thr Thr
            20                  25                  30

Gln Ala Thr Val Pro Ala Gly Thr Val Val Thr Gly Ser Met Val Pro
        35                  40                  45

```
Arg Glu Pro Gly Val Ile Ala Gly Val Asp Val Ala Leu Leu Val Leu
    50                  55                  60

Asp Glu Val Phe Gly Val Asp Gly Tyr Arg Val Leu Tyr Arg Val Glu
65                  70                  75                  80

Asp Gly Ala Arg Leu Gln Ser Gly Gln Pro Leu Leu Thr Val Gln Ala
                85                  90                  95

Ala Ala Arg Gly Leu Leu Thr Ala Glu Arg Thr Met Leu Asn Leu Val
            100                 105                 110

Cys His Met Ser Gly Ile Ala Thr Val Thr Ala Trp Val Asp Ala
            115                 120                 125

Val Arg Gly Thr Lys Ala Lys Ile Arg Asp Thr Arg Lys Thr Leu Pro
        130                 135                 140

Gly Leu Arg Ala Leu Gln Lys Tyr Ala Val Arg Val Gly Gly Gly Val
145                 150                 155                 160

Asn His Arg Leu Gly Leu Gly Asp Thr Ala Leu Ile Lys Asp Asn His
                165                 170                 175

Val Ala Ala Val Gly Ser Val Val Asp Ala Leu Arg Ala Val Arg Ala
            180                 185                 190

Ala Ala Pro Glu Leu Pro Cys Glu Val Glu Val Asp Ser Leu Glu Gln
        195                 200                 205

Leu Asp Ala Met Leu Ala Glu Glu Pro Glu Leu Ile Leu Leu Asp Asn
    210                 215                 220

Phe Pro Val Trp Gln Thr Gln Val Ala Val Gln Arg Arg Asp Ile Arg
225                 230                 235                 240

Ala Pro Thr Val Leu Leu Glu Ser Ser Gly Gly Leu Ser Leu Glu Asn
                245                 250                 255

Ala Ala Ile Tyr Ala Gly Thr Gly Val Asp Tyr Leu Ala Val Gly Ala
            260                 265                 270

Leu Thr His Ser Val Arg Ile Leu Asp Ile Gly Leu Asp Leu
        275                 280                 285

<210> SEQ ID NO 6
<211> LENGTH: 297
<212> TYPE: PRT
<213> ORGANISM: Salmonella typhimurium

<400> SEQUENCE: 6

Met Pro Pro Arg Arg Tyr Asn Pro Asp Asp Arg Arg Asp Ala Leu Leu
1               5                   10                  15

Glu Arg Ile Asn Leu Asp Ile Pro Ala Ala Val Ala Gln Ala Leu Arg
            20                  25                  30

Glu Asp Leu Gly Gly Glu Val Asp Ala Gly Asn Asp Ile Thr Ala Gln
        35                  40                  45

Leu Leu Pro Ala Asp Thr Gln Ala His Ala Thr Val Ile Thr Arg Glu
    50                  55                  60

Asp Gly Val Phe Cys Gly Lys Arg Trp Val Glu Val Phe Ile Gln
65                  70                  75                  80

Leu Ala Gly Asp Asp Val Arg Leu Thr Trp His Val Asp Asp Gly Asp
                85                  90                  95

Ala Ile His Ala Asn Gln Thr Val Phe Glu Leu Asn Gly Pro Ala Arg
            100                 105                 110

Val Leu Leu Thr Gly Glu Arg Thr Ala Leu Asn Phe Val Gln Thr Leu
        115                 120                 125

Ser Gly Val Ala Ser Glu Val Arg Arg Tyr Val Gly Leu Leu Ala Gly
```

```
                130                 135                 140
Thr Gln Thr Gln Leu Leu Asp Thr Arg Lys Thr Leu Pro Gly Leu Arg
145                 150                 155                 160

Thr Ala Leu Lys Tyr Ala Val Leu Cys Gly Gly Ala Asn His Arg
                165                 170                 175

Leu Gly Leu Thr Asp Ala Phe Leu Ile Lys Glu Asn His Ile Ile Ala
                180                 185                 190

Ser Gly Ser Val Arg Gln Ala Val Glu Lys Ala Phe Trp Leu His Pro
                195                 200                 205

Asp Val Pro Val Glu Val Glu Asn Leu Asp Glu Leu Asp Asp
210                 215                 220

Ala Leu Lys Ala Gly Ala Asp Ile Ile Met Leu Asp Asn Phe Asn Thr
225                 230                 235                 240

Asp Gln Met Arg Glu Ala Val Lys Arg Val Asn Gly Gln Ala Arg Leu
                245                 250                 255

Glu Val Ser Gly Asn Val Thr Ala Glu Thr Leu Arg Glu Phe Ala Glu
                260                 265                 270

Thr Gly Val Asp Phe Ile Ser Val Gly Ala Leu Thr Lys His Val Arg
                275                 280                 285

Ala Leu Asp Leu Ser Met Arg Phe Cys
                290                 295

<210> SEQ ID NO 7
<211> LENGTH: 297
<212> TYPE: PRT
<213> ORGANISM: Escherichia coli

<400> SEQUENCE: 7

Met Pro Pro Arg Arg Tyr Asn Pro Asp Thr Arg Arg Asp Glu Leu Leu
1               5                   10                  15

Glu Arg Ile Asn Leu Asp Ile Pro Gly Ala Val Ala Gln Ala Leu Arg
                20                  25                  30

Glu Asp Leu Gly Gly Thr Val Asp Ala Asn Asn Asp Ile Thr Ala Lys
            35                  40                  45

Leu Leu Pro Glu Asn Ser Arg Ser His Ala Thr Val Ile Thr Arg Glu
50                  55                  60

Asn Gly Val Phe Cys Gly Lys Arg Trp Val Glu Val Phe Ile Gln
65                  70                  75                  80

Leu Ala Gly Asp Asp Val Thr Ile Ile Trp His Val Asp Asp Gly Asp
                85                  90                  95

Val Ile Asn Ala Asn Gln Ser Leu Phe Glu Leu Glu Gly Pro Ser Arg
                100                 105                 110

Val Leu Leu Thr Gly Glu Arg Thr Ala Leu Asn Phe Val Gln Thr Leu
            115                 120                 125

Ser Gly Val Ala Ser Lys Val Arg His Tyr Val Glu Leu Leu Glu Gly
            130                 135                 140

Thr Asn Thr Gln Leu Leu Asp Thr Arg Lys Thr Leu Pro Gly Leu Arg
145                 150                 155                 160

Ser Ala Leu Lys Tyr Ala Val Leu Cys Gly Gly Ala Asn His Arg
                165                 170                 175

Leu Gly Leu Ser Asp Ala Phe Leu Ile Lys Glu Asn His Ile Ile Ala
                180                 185                 190

Ser Gly Ser Val Arg Gln Ala Val Glu Lys Ala Ser Trp Leu His Pro
                195                 200                 205
```

```
Asp Ala Pro Val Glu Val Glu Asn Leu Glu Leu Asp Glu
    210             215             220
Ala Leu Lys Ala Gly Ala Asp Ile Ile Met Leu Asp Asn Phe Glu Thr
225             230             235             240
Glu Gln Met Arg Glu Ala Val Lys Arg Thr Asn Gly Lys Ala Leu Leu
                245             250             255
Glu Val Ser Gly Asn Val Thr Asp Lys Thr Leu Arg Glu Phe Ala Glu
            260             265             270
Thr Gly Val Asp Phe Ile Ser Val Gly Ala Leu Thr Lys His Val Gln
        275             280             285
Ala Leu Asp Leu Ser Met Arg Phe Arg
290             295

<210> SEQ ID NO 8
<211> LENGTH: 297
<212> TYPE: PRT
<213> ORGANISM: Homo sapiens

<400> SEQUENCE: 8

Met Asp Ala Glu Gly Leu Ala Leu Leu Pro Pro Val Thr Leu Ala
1               5              10              15
Ala Leu Val Asp Ser Trp Leu Arg Glu Asp Cys Pro Gly Leu Asn Tyr
            20              25              30
Ala Ala Leu Val Ser Gly Ala Gly Pro Ser Gln Ala Ala Leu Trp Ala
        35              40              45
Lys Ser Pro Gly Val Leu Ala Gly Gln Pro Phe Phe Asp Ala Ile Phe
    50              55              60
Thr Gln Leu Asn Cys Gln Val Ser Trp Phe Leu Pro Glu Gly Ser Lys
65              70              75              80
Leu Val Pro Val Ala Arg Val Ala Glu Val Arg Gly Pro Ala His Cys
                85              90              95
Leu Leu Leu Gly Glu Arg Val Ala Leu Asn Thr Leu Ala Arg Cys Ser
            100             105             110
Gly Ile Ala Ser Ala Ala Ala Ala Val Glu Ala Ala Arg Gly Ala
        115             120             125
Gly Trp Thr Gly His Val Ala Gly Thr Arg Lys Thr Thr Pro Gly Phe
    130             135             140
Arg Leu Val Glu Lys Tyr Gly Leu Leu Val Gly Gly Ala Ala Ser His
145             150             155             160
Arg Tyr Asp Leu Gly Gly Leu Val Met Val Lys Asp Asn His Val Val
                165             170             175
Ala Ala Gly Gly Val Glu Lys Ala Val Arg Ala Ala Arg Gln Ala Ala
            180             185             190
Asp Phe Ala Leu Lys Val Glu Val Glu Cys Ser Ser Leu Gln Glu Ala
        195             200             205
Val Gln Ala Ala Glu Ala Gly Ala Asp Leu Val Leu Leu Asp Asn Phe
    210             215             220
Lys Pro Glu Glu Leu His Pro Thr Ala Thr Val Leu Lys Ala Gln Phe
225             230             235             240
Pro Ser Val Ala Val Glu Ala Ser Gly Gly Ile Thr Leu Asp Asn Leu
                245             250             255
```

-continued

Pro Gln Phe Cys Gly Pro His Ile Asp Val Ile Ser Met Gly Met Leu
            260                 265                 270

Thr Gln Ala Ala Pro Ala Leu Asp Phe Ser Leu Lys Leu Phe Ala Lys
        275                 280                 285

Glu Val Ala Pro Val Pro Lys Ile His
    290                 295

<210> SEQ ID NO 9
<211> LENGTH: 295
<212> TYPE: PRT
<213> ORGANISM: Saccharomyces cerevisiae

<400> SEQUENCE: 9

Met Pro Val Tyr Glu His Leu Leu Pro Val Asn Gly Ala Trp Arg Gln
1               5                   10                  15

Asp Val Thr Asn Trp Leu Ser Glu Asp Val Pro Ser Phe Asp Phe Gly
            20                  25                  30

Gly Tyr Val Val Gly Ser Asp Leu Lys Glu Ala Asn Leu Tyr Cys Lys
        35                  40                  45

Gln Asp Gly Met Leu Cys Gly Val Pro Phe Ala Gln Glu Val Phe Asn
    50                  55                  60

Gln Cys Glu Leu Gln Val Glu Trp Leu Phe Lys Glu Gly Ser Phe Leu
65                  70                  75                  80

Glu Pro Ser Lys Asn Asp Ser Gly Lys Ile Val Val Ala Lys Ile Thr
                85                  90                  95

Gly Pro Ala Lys Asn Ile Leu Leu Ala Glu Arg Thr Ala Leu Asn Ile
            100                 105                 110

Leu Ser Arg Ser Ser Gly Ile Ala Thr Ala Ser His Lys Ile Ile Ser
        115                 120                 125

Leu Ala Arg Ser Thr Gly Tyr Lys Gly Thr Ile Ala Gly Thr Arg Lys
    130                 135                 140

Thr Thr Pro Gly Leu Arg Arg Leu Glu Lys Tyr Ser Met Leu Val Gly
145                 150                 155                 160

Gly Cys Asp Thr His Arg Tyr Asp Leu Ser Ser Met Val Met Leu Lys
                165                 170                 175

Asp Asn His Ile Trp Ala Thr Gly Ser Ile Thr Asn Ala Val Lys Asn
            180                 185                 190

Ala Arg Ala Val Cys Gly Phe Ala Val Lys Ile Glu Val Glu Cys Leu
        195                 200                 205

Ser Glu Asp Glu Ala Thr Glu Ala Ile Glu Ala Gly Ala Asp Val Ile
    210                 215                 220

Met Leu Asp Asn Phe Lys Gly Asp Gly Leu Lys Met Cys Ala Gln Ser
225                 230                 235                 240

Leu Lys Asn Lys Trp Asn Gly Lys Lys His Phe Leu Leu Glu Cys Ser
                245                 250                 255

Gly Gly Leu Asn Leu Asp Asn Leu Glu Glu Tyr Leu Cys Asp Asp Ile
            260                 265                 270

Asp Ile Tyr Ser Thr Ser Ser Ile His Gln Gly Thr Pro Val Ile Asp
        275                 280                 285

Phe Ser Leu Lys Leu Ala His
    290                 295